(12) United States Patent
Shastri et al.

(10) Patent No.: US 6,190,893 B1
(45) Date of Patent: Feb. 20, 2001

(54) ELECTROACTIVE MATERIALS FOR STIMULATION OF BIOLOGICAL ACTIVITY OF BONE MARROW STROMAL CELLS

(75) Inventors: Venkatram R. Shastri, Allston; Nahid Rahman; Ivan Martin, both of Cambridge; Robert S. Langer, Jr., Newton, all of MA (US)

(73) Assignee: Massachusetts Institute of Technology, Cambridge, MA (US)

(*) Notice: Under 35 U.S.C. 154(b), the term of this patent shall be extended for 0 days.

(21) Appl. No.: 09/156,317

(22) Filed: Sep. 18, 1998

(51) Int. Cl.$^7$ .................................................. C12N 13/00
(52) U.S. Cl. ........................................................ 435/173.8
(58) Field of Search .......................................... 435/173.8

(56) References Cited

U.S. PATENT DOCUMENTS

| | | | |
|---|---|---|---|
| 4,904,259 | * 2/1990 | Itay | 623/16 |
| 5,599,676 | * 2/1997 | Vonderheide et al. | 435/7.2 |
| 5,658,761 | * 8/1997 | Thalmeier et al. | 435/69.4 |
| 5,843,741 | * 12/1998 | Wong et al. | 435/173.8 |
| 6,095,148 | 8/2000 | Shastri et al. | 128/898 |

FOREIGN PATENT DOCUMENTS

| | | |
|---|---|---|
| WO89/03876 | 5/1989 | (WO). |
| WO 97/16545 | 5/1997 | (WO). |

OTHER PUBLICATIONS

Bassett et al., "Augmentation of Bone Repair by Inductively Coupled Electromagnetic Fields", *Science*, 1974, 184, 575.
Bassett et al., "Effects of Electric Current on Bone in vivo", *Nature*, 1964, 204, 652.
Becker et al., "Clinical Experiences with Low Intensity Direct Current Stimulation of Bone Growth", *Clinical Orthopaedics and Related Research*, 1977, 124, 75.
Brighton et al., "Treatment of Nonunion with Constant Direct Current", *Clinical Orthopaedics and Related Research*, 1977, 124, 106.
Brighton et al., "In Vitro Bone–Cell Response to a Capacitively Coupled Electric Field" in *Basic Science and Pathology, Clinical Orthopaedics and Related Research*, 1992, 285, 255.
Hambury et al., "Effect of Microamp Electrical Currents on Bone in vivo and its Measurement Using Strontium–85 Uptake", *Nature*, 1971, 231, 190.
Korenstein et al., "Capacitative Pulsed Electric Stimulation of Bone Cells Induction of Cyclic–AMP Changes and DNA Synthesis", *Biochimica et Biophysica Acta*, 1984, 803, 302.
Langer et al., "Tissue Engineering", *Science*, 1993, 260, 920.
Marino et al., "Quasi–Static Charge Interactions in Bone", *Journal of Electrostatics*, 1988, 21, 347.

Ozawa et al., "Electric Fields Stimulate DNA Synthesis of Mouse Osteoblast–Like Cells (MC3T3–E1) by a Mechanism Involving Calcium Ions", *Journal of Cellular Physiology*, 1989, 138, 477.
Peppas et al., "New Challenges in Biomaterials", *Science*, 1994, 263, 1715.
Scakenraad et al., "The Influence of Substratum Surface Free Energy on Growth and Spreading of Human Fibroblasts in the Presence and Absence of Serum Proteins", *Journal of Biomedical Materials Research*, 1986, 20, 773.
Shamoz, M.H., "Experimental Model for Studying the Effect of Electric Current on Bone in vivo", *Nature*, 1969, 224, 1112.
Williams et al., "Piezoelectricity and Inhomogeneity in Ceramics, Polymers and Bone" *Ferroelectrics*, 1983, 51, 61.
Wong et al., "Electrically Conducting Polymers Can Noninvasively Control the Shape and Growth of Mammalian Cells", *Proc. Natl. Acad. Sci. USA*, 1994, 91, 3201.
Shastri, et al., "Biomedical Applications of Electroactive Polymers," *Electrical and Optical Polymer Systems* (Wise, et al., eds) New York; Marcel Dekker (1998) pp. 1031–1051.
Aoki, et al., "Secretory Function of Adrenal Chromaffin Cells Cultured on Polypyrrole Films," Biomaterials, 17 (20):1971–1974 (1996).
Luben, R.A. "Effects of Low–Energy Electromagnetic Fields (Pulsed and DC) on Membrane Signal Transduction Processes in Biological Systems," *Health Physics*, 61 (1): 15–28 (1991).

* cited by examiner

Primary Examiner—Jon P. Weber
(74) Attorney, Agent, or Firm—Choate, Hall & Stewart

(57) ABSTRACT

Compositions, methods and systems are provided for the stimulation of biological activities within bone marrow stromal cells by applying electromagnetic stimulation to an electroactive material, wherein the electromagnetic stimulation is coupled to the electromagnetic material. In general the present invention involves attaching or associating the desired bone marrow stromal cells to or with a surface comprising an electroactive material, and applying electromagnetic radiation directly to the desired area. In preferred embodiments, the stimulation of biological activities within bone marrow stromal cells results from inducing one or more activities including, but not limited to, gene expression, cell growth, cell differentiation, signal transduction, membrane permeability, cell division and cell signalling. In particularly preferred embodiments, the present invention stimulates bone cell regeneration. In exemplary embodiments, the electroactive materials used in the present invention are either two-dimensional substrates such as thin films having at least one surface of an electroactive material, or in alternative embodiments, the electroactive materials are three-dimensional substrates comprising a matrix having at least one surface of an electroactive material.

59 Claims, 22 Drawing Sheets

Poly(styrenesulfonate)
PSS

|||||||||| Type 1 PSS ooooooooooo Type 2 PSS

∿∿∿∿∿∿∿ Type 3 PSS

⟵ 100 μm ⟶

A

B

C

|← 100 um →|

A

B

100 μm

Au wire (reference electrode)
Bone marrow stromal cells and medium
Ag wire (counter electrode)
PPy or ITO (working electrode)

Ag wire (counter electrode)
BMSC and medium
Au wire (reference electrode)
PPy or ITO (Working Electrode)

ELECTROACTIVE MATERIALS FOR STIMULATION OF BIOLOGICAL ACTIVITY OF BONE MARROW STROMAL CELLS

GOVERNMENT SUPPORT

The government has rights in this invention pursuant to National Science Foundation Grant Number 9525913.

BACKGROUND OF THE INVENTION

Tissue engineering is a field in which the principles of biology, engineering, and materials science are applied to the development of functional substitutes for damaged tissue. (See, Langer, et al., "Tissue Engineering", Science, 1993, 260, 920). In general, three different strategies have been adopted for the creation of new tissue: (i) isolated cells or cell substrates, in which only those cells that supply the needed function are replaced; (ii) tissue-inducing substances, such as signal molecules and growth factors, and (iii) cells placed on or within matrices. Researchers have been interested in applying these novel techniques to find replacements for tissues such as ectodermal, endodermal, and mesodermal-derived tissue. In particular, researchers are invested the replacement of tissues in the nervous system, cornea, skin, liver, pancreas, cartilage, bone, and muscle to name a few.

One specific area of interest for the use of tissue engineering techniques is in bone regeneration and repair. Over 1 million surgical procedures in the United States each year involve bone repair. Bone defects can result from diverse causes such as trauma, birth defects and disease pathoses. Current methods rely on an adequate supply of autogenous (from a donor site) and/or allogenic (from a human cadaver) bone. However, removal of autogenous bone for the grafting procedure requires surgery at a second site and also involves blood loss, pain and increased morbidity. Furthermore, for allografts, there exists the potential for disease transmission or host rejection. Thus, the search for alternatives to autografts and allografts in bone repair and regeneration remains an important topic in medical research.

A variety of biologically compatible materials have been tested for use in bone repair. The materials include naturally occurring compounds such as tricalcium phosphate or hydroxyapatite porous ceramics (Yoshikawa et al., *Biomed. Mater. Eng.*, 1997, 7, 49; Ohgushi et al., *J Biomed. Mat. Res.*, 1990, 24, 1563), and synthetic materials including absorbable lactide and glycolide polymers (Ishaug, et al., *J Biomed. Mater. Res.*, 1997, 36, 17; Ashammakhi et al., *Biomaterials*, 1996, 18, 3), and ceramic bioglasses (Yamamuro, T., *Bone-bonding behavior and clinical use of A-W glass-ceramic, in Bone Grafts, Derivatives and Substitutes*, M. Urist, O'Connor, B. T., Burwell, R. G., Ed. 1994, Butterworth-Heinemann: Oxford U.K.). The existing technology, using biomaterials, though effective in many cases, is still beset with numerous difficulties and disadvantages. Thus, there still remains a need for improved methods in treating bone defects.

In 1953, Yasuda discovered an interesting property in bone (Yasuda, I., *J Kyoto Med. Soc.*, 1952, 4, 395). He first reported that upon mechanical deformation of bone, electricity was produced upon mechanical deformation of bone, a phenomenon known as the "piezoelectric" effect. He showed that the mechanical loading of bone induced electromagnetic potentials or fields that could alter bone metabolism and produce an increase in bone mass and/or structure (Yasuda, I., *J Kyoto Pref Univ. Med.*, 1953, 53, 325). Fukada, Becker, Bassett and others have suggested that the electrical activity observed in bone is a probable mediator of its repair and adaptive remodeling in response to mechanical loading (FIG. 1) (Fukada et al., *J Phys. Soc. Japan*, 1957, 12, 1158; Becker et al., "The Bioelectric Factors of Controlling Bone Structure", in Bone Biodynamics, R. Bourne, Ed., 1964, Little, Brown and Co.: New York; Bassett et al., *Nature*, 1964, 204, 652). Furthermore, these authors have observed that an exogenous electrical stimulus alone can stimulate bone regeneration (Lavine et al., *Nature*, 1969, 224, 1112; Humbury et al., *Nature*, 1971, 231, 190; Becker et al., *Clin. Orthop. Rel. Res.*, 1977, 129, 75; Bassett et al., *Clin. Orthop. Rel. Res.*, 1977, 124, 128; Brighton et al., *Clin. Orthop. Relat. Res.*, 1977, 124, 106; Watson et al., *Jap. J Appl. Phys.*, 1978, 17, 215; Bassett et al., *Science*, 1979, 184, 575). The early success of these experiments with direct current and electromagnetic induction finally led to widespread clinical treatments of non-union bone fractures. However, localization of the electrical stimulation, which is critical to effective treatment, still remains a challenge (Spadaro, J. A., *Bioelectromagnetics*, 1997, 18, 193). Therefore, a system whereby one can externally control and regulate the stimulus would be extremely attractive.

Clearly, there remains a need to develop systems and methods whereby biological activities of cells, such as, but not limited to cell growth, can be stimulated by direct application of electromagnetic stimulation. This would be particularly important in applications to tissue engineering.

SUMMARY OF THE INVENTION

The concept of "tissue engineering" comes into play in the present invention for the development a system in which the biological activities of cells can be stimulated. An interesting class of synthetic polymers explored previously by Langer and co-workers as three-dimensional matrices that can take advantage of these properties are the electrically conducting or electroactive polymers. Based on their ability to respond to electrical or electromagnetic stimuli, they can act as an interface between the external and physiological environments of a connective tissue such as bone, which is capable of undergoing repair and regeneration on exposure to the same stimuli (Shastri et al., "Biomedical Applications of Electroactive Polymers", in *Electrical and Optical Polymer Systems*, D. L. Wise, Wnek, G. E., Trantolo, D. J., Cooper, T. M., Gresser, J. D., Ed., 1998 Marcel Dekker: New York, 1031).

The present invention provides compositions, methods and systems for the stimulation of biological activities within cells by applying electromagnetic stimulation to an electroactive material, wherein the electromagnetic stimulation is coupled to the electroactive material. The present invention provides methods for the stimulation of biological activities within cells, which involves attaching or associating the desired cells to or with a surface comprising an electroactive material, and applying electromagnetic stimulation directly to the desired area. In preferred embodiments, the stimulation of biological activities within cells results from inducing one or more activities including, but not limited to, gene expression, cell growth, cell differentiation, signal transduction, membrane permeability, cell division, and cell signalling. In exemplary embodiments, the electroactive materials are either two-dimensional substrates or three-dimensional substrates comprising a matrix having at least one surface of an electroactive material.

In one preferred embodiment, the present invention provides a method for stimulating one or more biological activities of cells comprising contacting cells with an electroactive substrate, wherein the electroactive substrate already has attached thereto, or associated therewith, mammalian tissue, and subsequently applying electromagnetic radiation at the location of the electroactive substrate, wherein the electromagnetic stimulation is coupled to the electromagnetic material. In another embodiment, a composition of cells and an electroactive substrate is first provided, wherein the electroactive substrate has at least one surface of electroactive material, and wherein the cells are attached thereto or associated with the electroactive substrate. Subsequently, the electromagnetic stimulation is applied to the composition in vitro, wherein the electromagnetic stimulation is coupled to the electromagnetic material and finally the composition is contacted with mammalian tissue to effect stimulation of cell function. In yet another embodiment, a composition of cells and an electroactive substrate is first provided, wherein the cells are attached thereto or associated with the electroactive substrate. Subsequently, the composition is then contacted with mammalian tissue, and finally the electromagnetic radiation is applied in vivo, wherein the electromagnetic stimulation is coupled to the electroactive material. In particularly preferred embodiments, the electromagnetic stimulation is coupled to the electroactive material by physical contact. In other embodiments, the electromagnetic stimulation is coupled to the electroactive material by electromagnetic induction.

In another aspect of the invention, a system is provided for stimulating one or more biological activities of cells comprising a composition comprising an electroactive substrate, wherein the electroactive substrate has at least one surface of electroactive material, and wherein the electroactive material has attached thereto, or associated therewith, one or more mammalian cells; and an apparatus for applying electromagnetic energy at the desired location.

Yet another aspect of the present invention is a two-dimensional stimulant of one or more biological activities of cells comprising one or more films of an electroactive substrate, wherein the one or more films are associated with or attached to one or more mammalian cells at a desired location. A three-dimensional stimulant of one or more biological activities of cells is also provided comprising an electroactive substrate associated with or attached to a matrix and wherein the electroactive substrate is associated with or attached to one or more mammalian cells at a desired location.

Definitions

"Electromagnetic Stimulation": As used herein, the term "electromagnetic stimulation" means any form of electromagnetic energy including, but not limited to, electromagnetic radiation or pulsed electromagnetic field stimulation (PEMF).

"Electroactive material": As used herein, the term "electroactive material" means a material that contains pockets of electron density. This material may be conducting, non-conducting, semiconducting, or piezoelectric, to name a few. For the purposes of the present invention, preferred electroactive materials include electroactive polymers. These electroactive polymers are characterized in that they contain at least a pocket of electron density and are capable of undergoing a phase transition upon subjecting the polymer to an electromagnetic field stimulus.

DESCRIPTION OF CERTAIN PREFERRED EMBODIMENTS

Recognizing the need to develop new methods in tissue engineering to directly affect cell activity, growth and/or function, the present invention provides compositions, methods and systems for the stimulation of biological activities within cells by applying electromagnetic stimulation to an electroactive material, wherein said electromagnetic stimulation is coupled to said electroactive material. In general, the present invention provides methods for the stimulation of biological activities within cells, which involves attaching or associating the desired cells to or with a surface comprising an electroactive material, and applying electromagnetic radiation directly to the desired area. In preferred embodiments, the stimulation of biological activities within cells results from inducing one or more activities including, but not limited to, gene expression, cell growth, cell differentiation, signal transduction, membrane permeability, cell division, and cell signalling. In exemplary embodiments, the electroactive materials are either two-dimensional substrates such as thin films having at least one surface of an electroactive material, or in alternative embodiments, the electroactive materials are three-dimensional substrates comprising a matrix, such as a polymer, and an electroactive material having at least one surface of an electroactive material.

Figure 1:
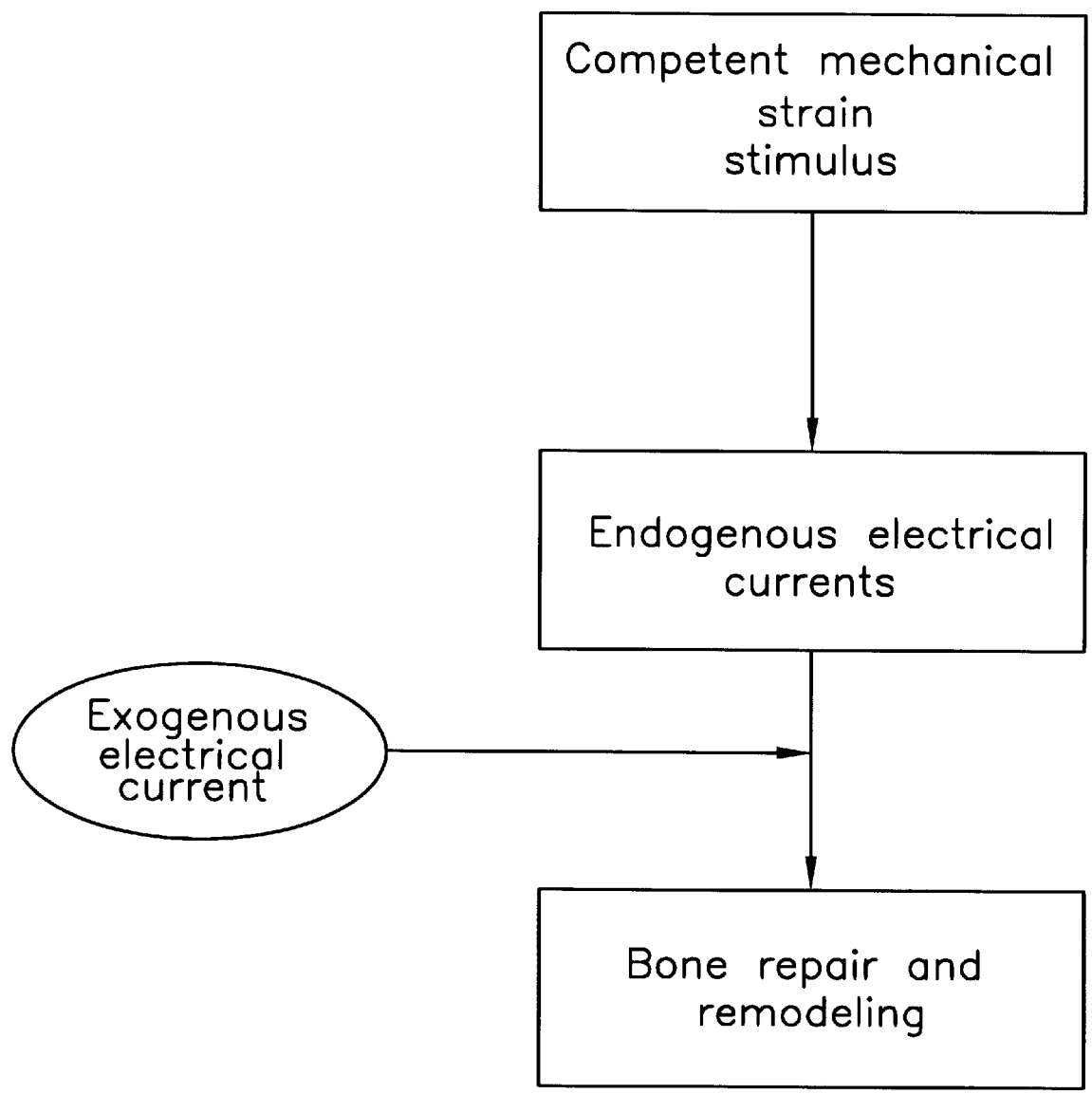
FIG. 1 depicts "Yasuda's hypothesis" (Modified from Spadaro, A. *Bioelectromagnetics*, 18:193–202, 1997).
Figure 2:
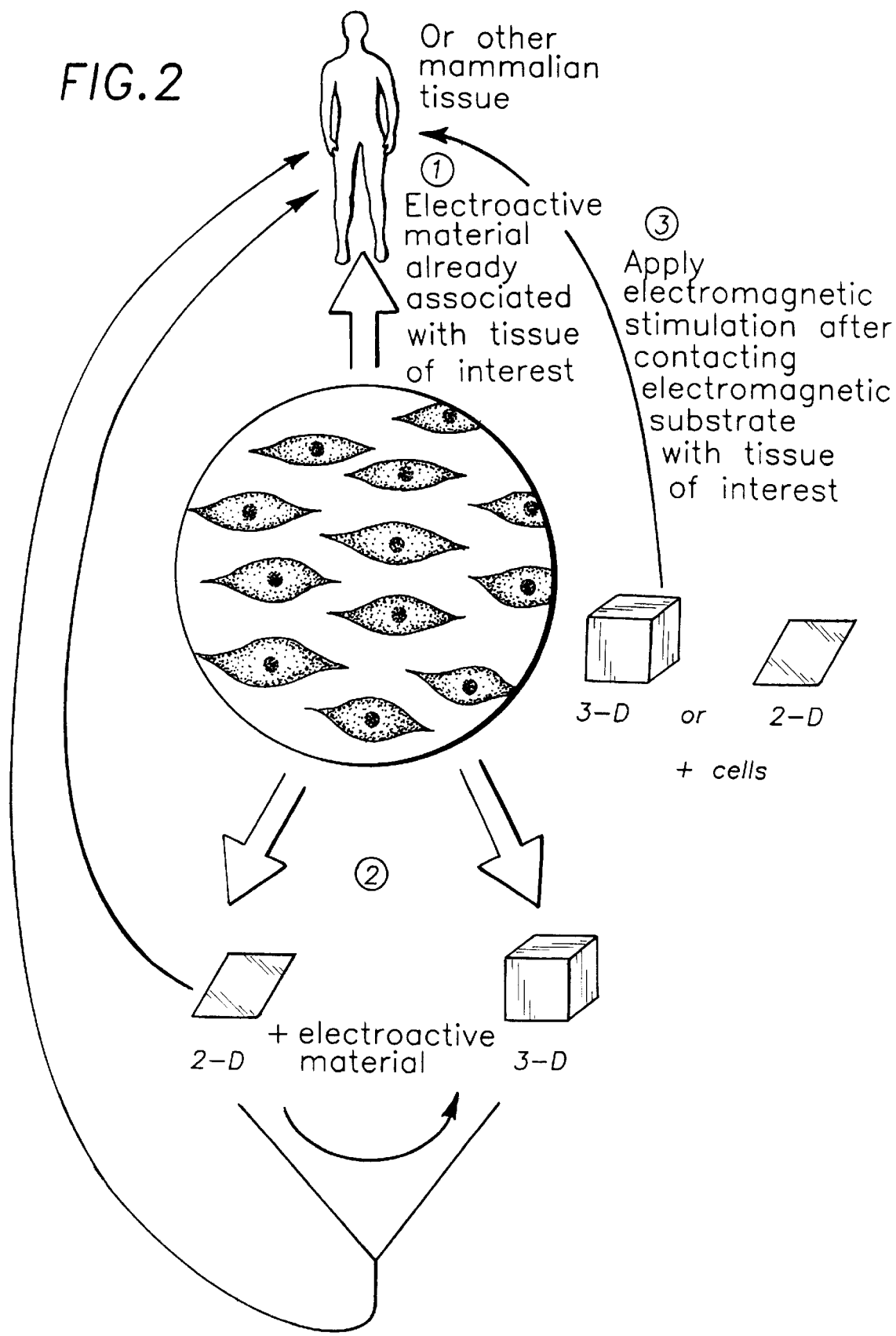
FIG. 2 depicts preferred embodiments for the method of the present invention.

As shown in FIG. 2, the inventive system can be applied using different methods. In one exemplary embodiment, as shown by the pathway labelled 1, cells are contacted with an electroactive substrate, which electroactive substrate already has attached thereto, or associated therewith, mammalian tissue, and subsequently applying electromagnetic radiation at the location of the electroactive substrate, the electromagnetic stimulation being coupled to the electromagnetic material. In another exemplary embodiment, as shown by the pathway labelled 2, a composition of cells and an electroactive substrate is first provided, which electroactive substrate has at least one surface of electroactive material, and wherein the cells are attached thereto or associated with the electroactive substrate. Subsequently, electromagnetic radiation is applied to the composition in vitro, wherein the electromagnetic stimulation is coupled to the electroactive material, and finally the composition is contacted with mammalian tissue to effect stimulation of cell function. In this particular embodiment, one of ordinary skill in the art will realize that, alternatively to contacting the composition including the cells and the electroactive substrate with the mammalian tissue, the cells can first be dissociated from the electroactive substrate after electromagnetic stimulation and then can be transferred to the tissue site of interest in the body (one or more mammalian cells). In yet another exemplary embodiment, as shown by the pathway labelled 3, a composition of cells and an electroactive substrate is first provided, wherein the electroactive substrate has at least one surface of electroactive material, and wherein the cells are attached thereto or associated with the electroactive substrate. Subsequently, the composition is then contacted with mammalian tissue, and finally the electromagnetic radiation is applied in vivo, wherein said electromagnetic stimulation is coupled to the electroactive material. In particularly preferred embodiments, the electromagnetic stimulation is coupled to the electroactive material by physical contact. In other embodiments, the electromagnetic stimulation is coupled to the electroactive material by electromagnetic induction.

In each of these embodiments, the electroactive materials for use in the present invention can be formulated as a two-dimensional substrate, for example, as a thin film of the substrate to which the desired cells are attached, or as a three-dimensional substrate, for example as a polymer coating on any three-dimensional matrix. Particularly preferred three-dimensional matrices include, but are not limited to polymers, biological polymers, and cellular solids, including, but not limited to, foam-like materials. The matrices used in the present invention are also preferably biodegradable.

Figure 3:
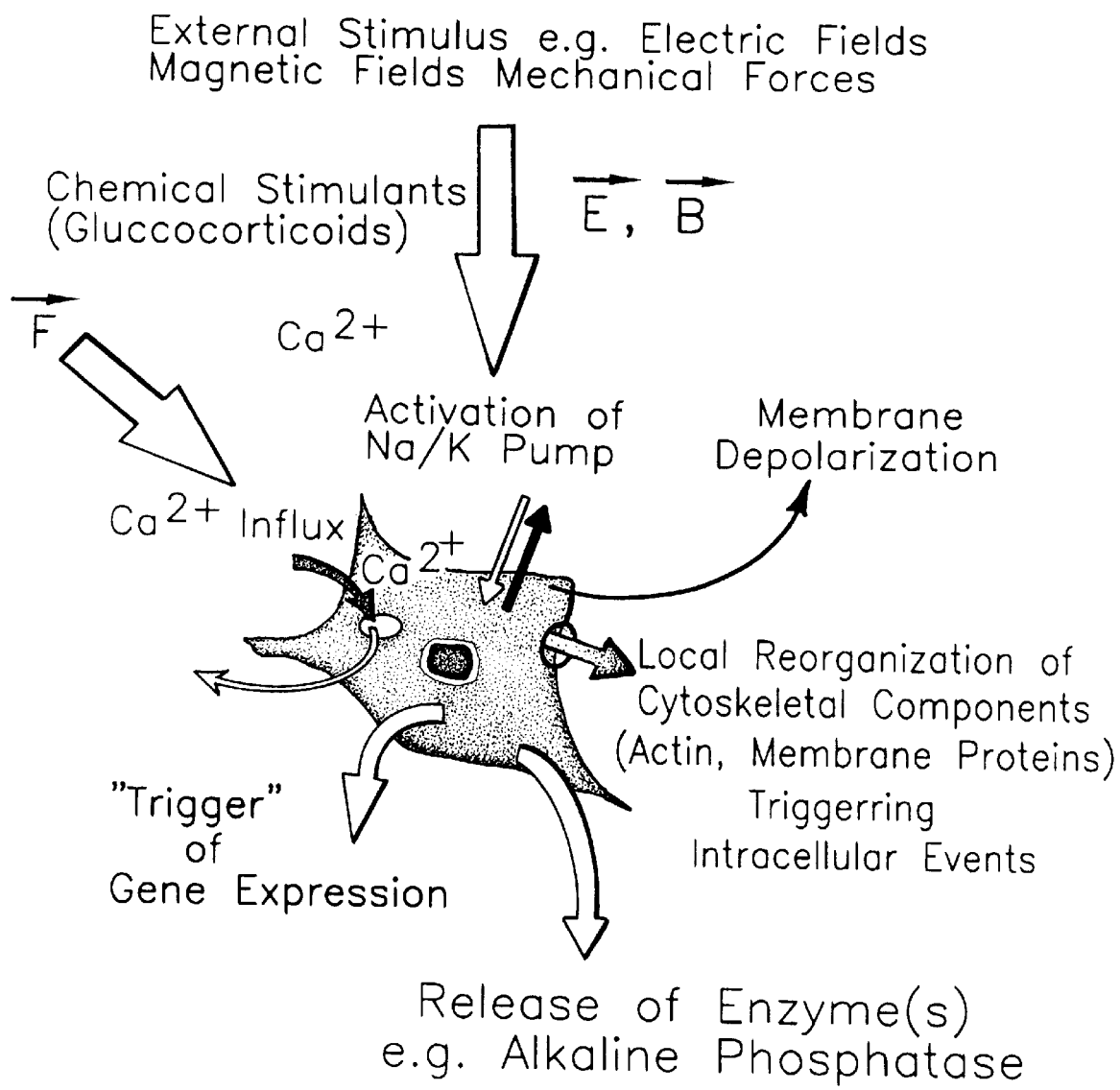
FIG. 3 depicts the effect of an external stimulus on cells.

Use of the inventive compositions, methods and systems enable the stimulation of one or more biological activities within cells by a variety of mechanisms (FIG. 3), such as, but not limited to, conformational changes in readsorbed proteins on the electroactive substrate upon electromagnetic stimulation, by electrophoretic redistribution of cytoskeletal components, by activation of voltage gated $Ca^{2+}$ and $Na/K$ ion channels, and by depolarization of membrane resting potentials. In particular, each of these are capable of affecting such biological activities within the cell such as, gene expression, cell growth, cell differentiation, cell signal transduction, and cell signalling, to name a few.

In preferred embodiments, cells are preferably mammalian cells selected from the group consisting of human cells, monkey cells, and mouse cells to name a few. Furthermore, the cells utilized for stimulation include, but are not limited to stem cells, and other cell lines resulting from the differentiation of pluripotent stem cells, for example, bone marrow stromal cells. Other preferred differentiated cells include muscle cells, cartilage cells, and connective tissue cells, to name a few. Preferred cells for use in the present invention are further characterized in that they are capable of responding to electrical fields, they are easily isolable for in vitro and in vivo studies, and they are not substantially contaminated by other cell types.

Figure 4:
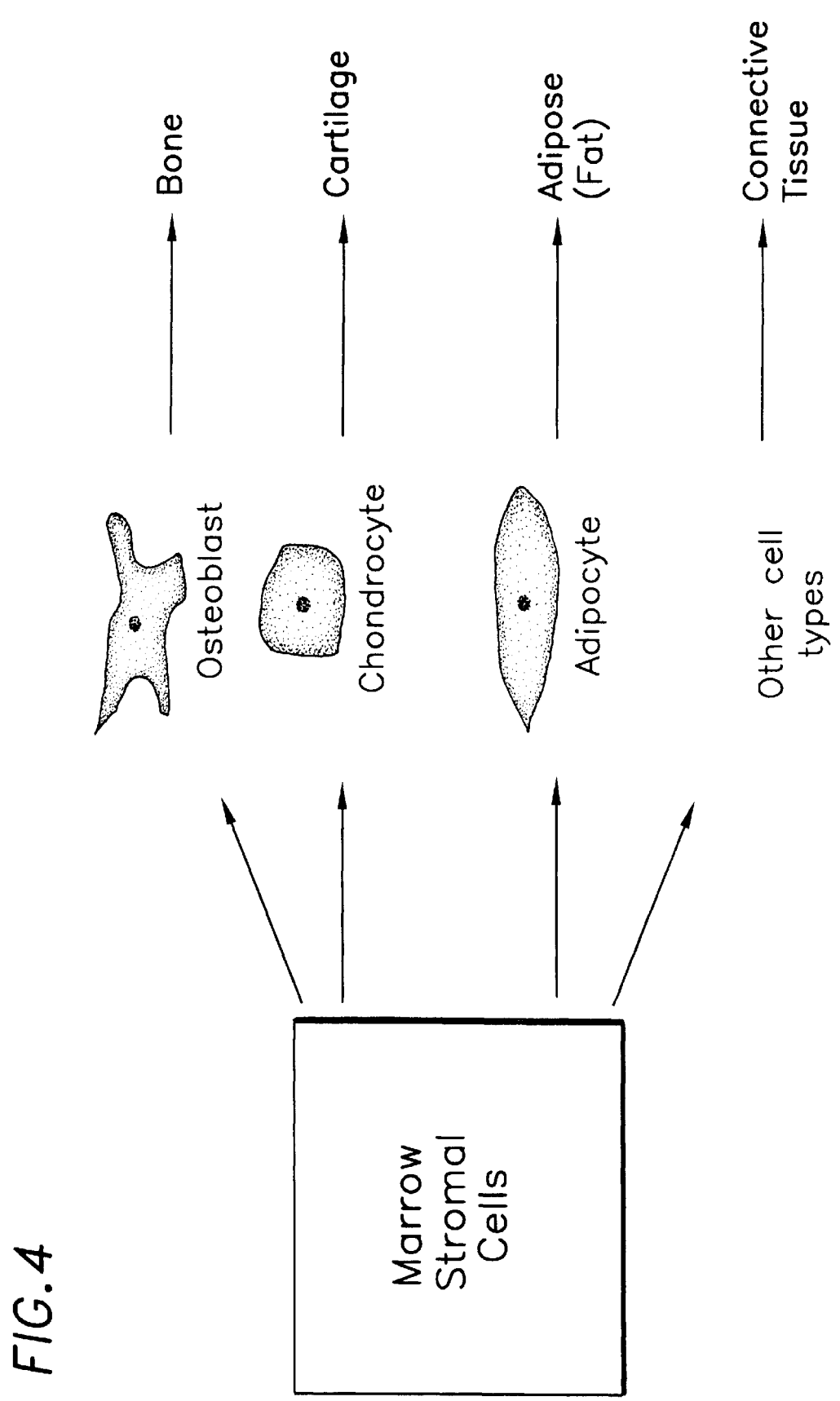
FIG. 4 illustrates a variety of end-stage phenotypes into which marrow stem cells may differentiate.

For the purposes of the present invention, stem cells are characterized in that they are not themselves terminally differentiated, they can divide without limit, and when they divide, each daughter cell has the choice of either remaining a stem cell, or embarking on a course leading irreversibly to terminal differentiation to become, in but one example, a bone marrow stromal cell. FIG. 4 shows that marrow stem cells are capable of differentiating though a series of separate and unique lineage transitions into a variety of end-stage phenotypes. According to the current hypothesis, there is a reservoir of cells in the marrow stromal system, which is associated with the soft connective tissues of marrow and bone surfaces. These cells have been shown to be pluripotent and are progenitor cells for a number of different cell lineages, including those of bone, cartilage, fat and fibrous tissues (FIG. 4).

In a particularly preferred embodiment, bone marrow stromal cells (BMSC) are utilized in the present invention. There is substantial evidence showing the bone marrow stromal cells, cultured either in vivo or in vitro, can induce bone formation in a variety of animal models. The results of these studies are consistent with the hypothesis that part of the renewal of the osteoblast population at bone surfaces involves the recruitment, proliferation and differentiation of these osteoprogenitor cells inhabiting the bone marrow, thus making BMSC a preferred system particularly for the study of osteogenesis and bone regeneration.

As discussed previously, in the inventive method, the cells are applied to an electroactive material. This application can occur prior to contacting the electroactive material with mammalian tissue, or after contacting the electroactive material with mammalian tissue. Particularly preferred electroactive materials for use in the present invention include electroactive polymers. As discussed above, electroactive polymers are utilized in the present invention because of their ability to respond to electromagnetic stimuli. Based upon this ability, they can act as an interface between the external and physiological environments of a connective tissue, such as bone, which is capable of undergoing repair and regeneration on exposure to the same stimuli. In but one example, electroactive polymers are able to exploit the piezoelectrical nature of bone and also act as interactive scaffolds for bone repair. In preferred embodiments the electroactive materials used in the present invention are also selected for their compatibility with the cells utilized.

In general, electroactive polymers comprise any polymer that contains a pocket of electron density and is capable of undergoing a phase transition upon subjecting the polymer to an electromagnetic field stimulus (See, for example, Shastri, V. R. and Pishko, M. V. "Biomedical Applications of Electroactive Polymers" in *Electrical and Optical Polymer Systems: Fundamentals, Methods and Applications*, Eds. D. L. Wise, D. J. Trantolo and G. E. Wnek, World Scientific Publishing Co., Chapter 30, 1031–1051 (1998)). Examples of specific electroactive polymers suitable for use in the present invention include, but are not limited to, conducting polymers, non-conducting polymers, piezoelectric polymers, semiconducting polymers, insulators, and substituted ionomer resins (ionons). The electroactive polymers of the present invention may be conductive, as for example, polypyrrole, or may alternatively be a polymer having a backbone substituted with electroactive moieties such as heme, porphyrin, or ferrocene. For example, ionomer resin, a copolymer of ethylene and a vinyl monomer with an acid group, contains positively and negatively charged groups suitable for substitution of other electroactive moieties. Other polymers that are conductive or that have regions of high electron density are suitable in the practice of the present invention and include, but are not limited to, poly (p-phenylene), poly(p-phenylene-vinylene), poly (thiophene), and poly(aniline). Another suitable polymer is hemosin, which is a polymer of heme, a component of hemoglobin. Other polymers particularly preferred for use in the present invention include intelligent polymers which include, but are not limited to gels, and polyacrylamide gels.

Particularly preferred electroactive polymers suitable for use in the present invention include conductive polymers. Interestingly, a key property of most polymers, which distinguishes them from metals, is their inability to conduct electricity. However, during the past 25 years, a new class of organic polymers has been devised with a remarkable ability to conduct electrical current. These electrically conducting polymers typically possess a conjugated backbone with a high degree of p-orbital overlap. Through a process known as "doping", the neutral polymer can be oxidized or reduced to become either positively charged (oxidative, p-type) or negatively charged (reductive, n-type). The generation and propagation of charge occurs via polarons or bipolarons along the oxidized polymer backbone. The conductive form of the polymer contains counterions that serve to maintain charge neutrality but do not affect the oxidation level of the polymer.

More particularly, the invention is described with reference to polypyrrole and its use in bone regeneration. This example is provided only for the purpose of illustration and is not intended to limit the scope of the present invention. As one of ordinary skill in the art will realize, the inventive compositions, methods and systems can be applied to a range of biological activities within cells and can employ a variety of electroactive materials to effect biological activities within cells.

Example: Use of Polypyrrole in the Present Invention

Figure 5:
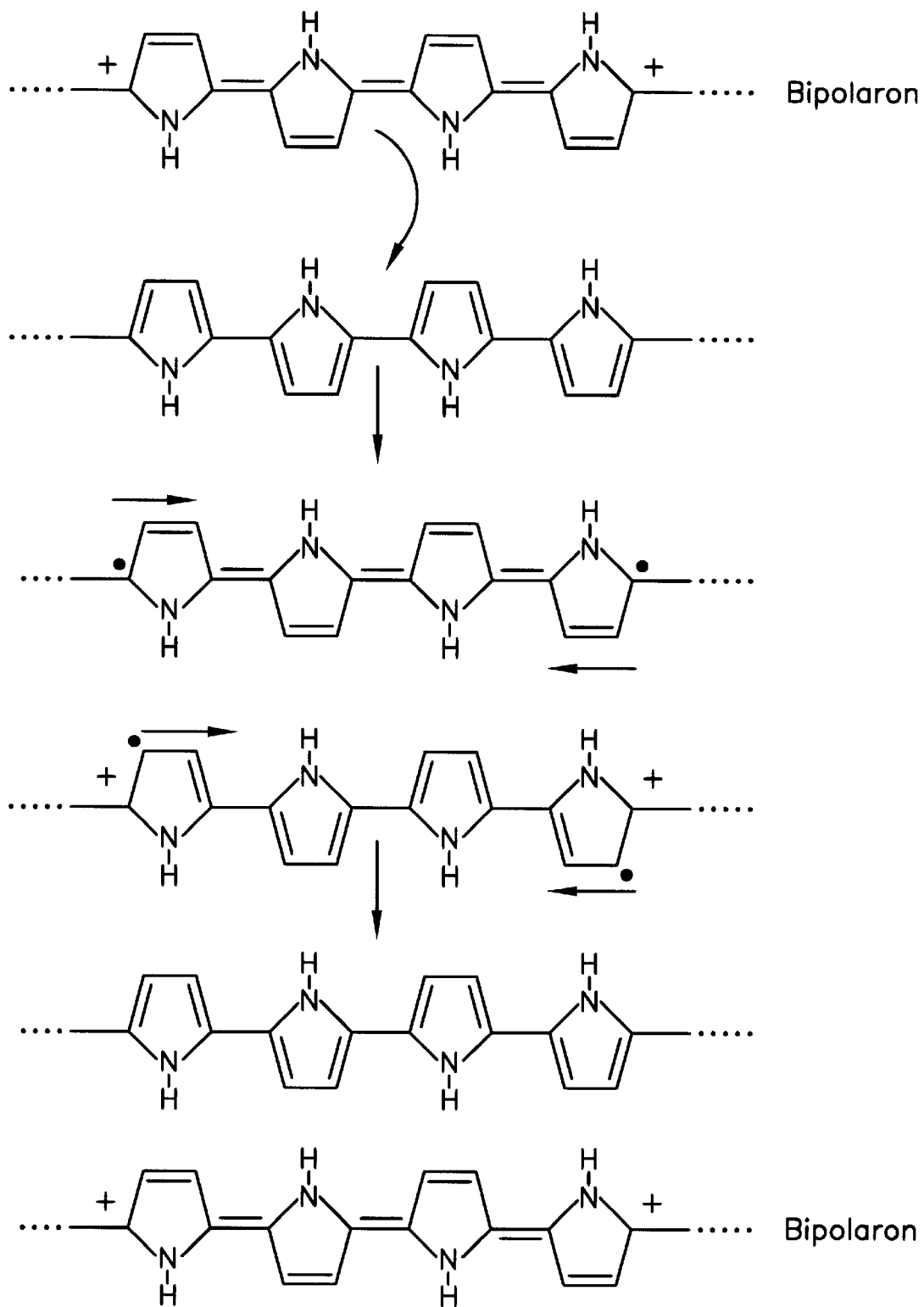
FIG. 5 depicts the mechanism of electronic conduction in oxidized polypyrrole (Ppy) via interchain hopping of bipolarons. (Reproduced from Shastri, V. R., *Evaluation of polypyrrole thin films as substratum for mammalian cell culture*, Troy, N.Y.: Rensselaer Polytechnic Institute, 1995).

In an exemplary embodiment, polypyrrole is employed for use in present invention, although one of ordinary skill in the art will realize that the following discussion can be applied to other abovementioned electroactive materials and electroactive polymers. Polypyrrole, which belongs to the class of aromatic poly(heterocyclics) has been extensively studied. It was first electrochemically synthesized by Diaz and co-workers (Diaz et al., *J Chem. Soc. Chem. Commun.*, 1979, 635), and can be synthesized both by chemical and electrochemical means. Through the "doping" process, charge neutrality is maintained by incorporating dopant ions into the polymer backbone. FIG. 5 shows the mechanism by which the electronic conduction in polypyrrole occurs. The neutral polymer chain is oxidized with the removal of electrons to form radical cations. The radical ions are delocalized over a portion of the backbone, creating a structural defect known as a polaron, which contains both spin and positive charge. Two polarons can diffuse together and combine spins to form a bond, leaving a bipolaron species. The positive charges on the polymer backbone act as charge carriers for electrical conduction. Conduction can either occur along segments of the conjugated chain, or though charges hopping between chains.

Polypyrrole has been studied extensively due to its chemical and thermal stability, ease of preparation and electroactivity. It has been evaluated for a number of applications, such as amperometric glucose sensors (Couves, L. D., *Synth. Met.*, 1989, 28, C761), creatinine microbiosensors (Osaka et al., *J. Electrochem. Soc.*, 1998, 145, 406), immobilized enzyme-based analyte detection systems (Guiseppi-Elie et al., *Mater. Res. Soc. Symp. Proc.*, 1996, 413, 439) and electrodes to obtain electrochemically controlled dopamine release (Miller et al., *Macromolecules*, 1987, 20, 1594; Zhou et al., *J. Electroanal. Chem.*, 1989, 261, 147). Furthermore, its in vitro compatibility with mammalian cells has been explored (Shastri, V. R., Evaluation of polypyrrole thin films as substratum for mammalian cell culture, 1995 Rensselaer Polytechnic Institute: Troy, N.Y.; Wong et al., *Proc. Natl. Acad. Sci.*, 1994, 91, 3201). From these studies, it has been shown that both cell-surface interactions and cellular functions on polypyrrole thin films could be controlled by either changing the oxidation state of the polymer or by changing the wettability of the polymer through the use of suitable dopants. Since surface characteristics such as charge density and wettability play a key role in protein-adsorption and cell-biomaterial interactions (Tamada et al., "Cell Attachment to Various Polymer Surfaces", in Polymers in Medicine II: Biomedical and Pharmaceutical Applications, P.G.E. Chiellini, Migliaresi, C., Nicolais, L., Ed., 1986: New York, 101; Schakenraad et al., *J. Biomed. Mater. Res.*, 1986, 20, 773; Shastri et al., *Mater. Res. Soc. Symp. Proc.*, 1996, 414, 113), it is desirable to engineer a material such as polypyrrole, that allows flexibility in predicting cellular behavior.

The synthesis and characterization of polypyrrole is described in Example 1. The surface properties of the PPy thin films were characterized by XPS. The surface composition of the PPy films at a take-off angle of 35 is shown in Table 1 below.

TABLE 1

| Atom | % Composition |
|---|---|
| O 1s | 25.81 |
| Na (Auger) | 5.21 |
| N 1s | 6.26 |
| C 1s | 59.40 |
| S 2p | 3.31 |
| N/S | 1.89 |
| Na/S | 1.57 |

Figure 6:
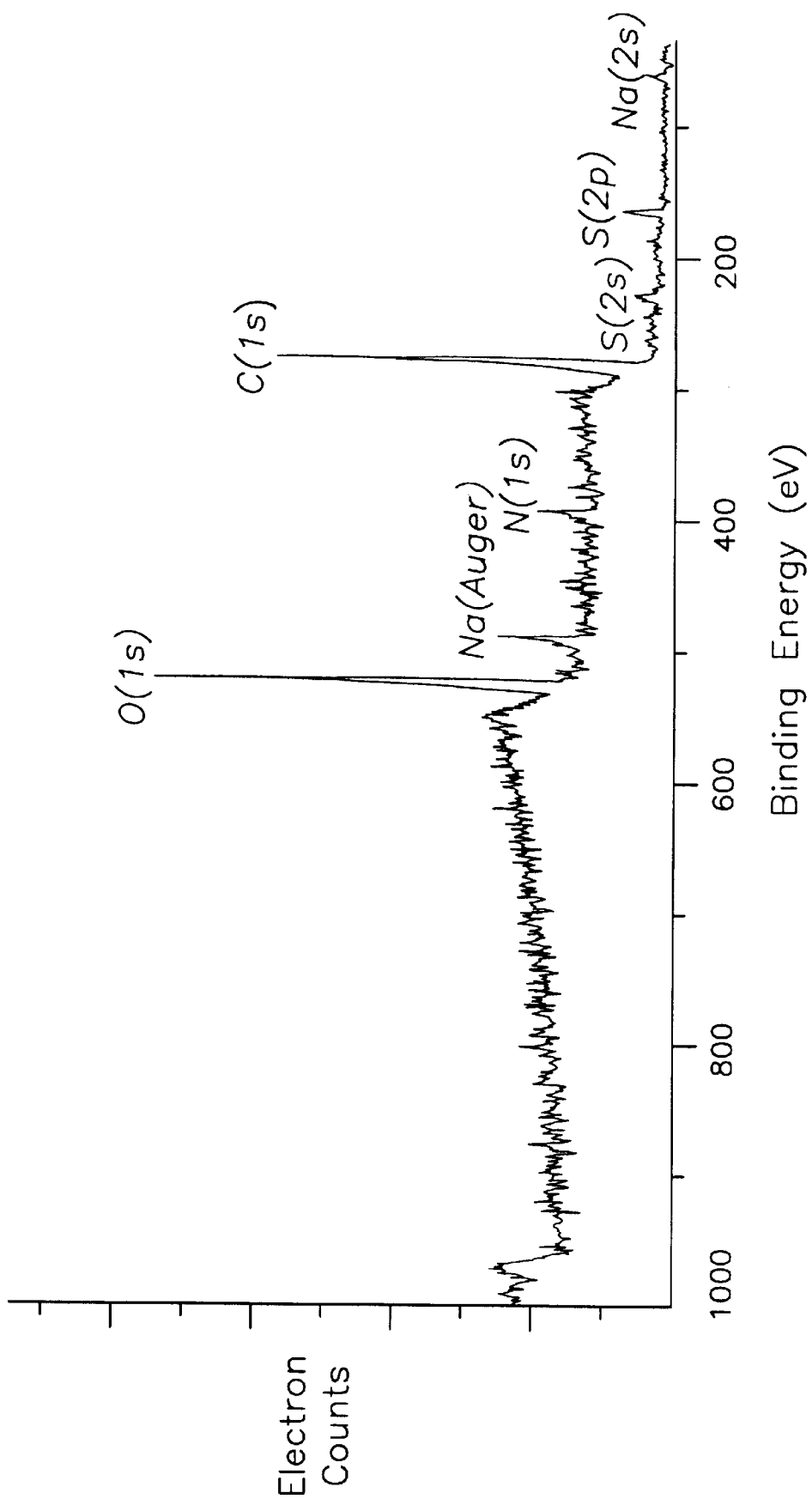
FIG. 6 depicts the XPS spectrum of PP-PSS thin film (0.1 $\mu$m thickness; x-ray spot size=1000 $\mu m^2$; electron flood gun energy=5 eV).

The corresponding XPS spectrum is shown in FIG. 6. The surface composition within a sampling depth of 10–100 Å indicates the presence of Na and S atoms from the sodium salt of poly(styrenesulfonate) (PSS) dopant. The surface N/S ratio was found to be consistent with results from comparable analysis depths (Beelen et al., *Synth. Met.*, 1991, 41 (Part I), 449; Neoh et al., *J. Phys. Chem. B*, 1997, 101, 726). That the surface is rich in negatively charged sulfonate groups is indicated by the presence of Na atoms, which are the associated cations with the pendant sulfonate group. The presence of the Na also indicates that the sulfonate groups are still in the salt form and were not protonated during the electrodeposition process. Furthermore, the almost 1:1 ratio of Na/S (1.57), demonstrates that the source of the Na is not merely a result of adsorbed ions in an electrical double layer, the layer formed at an electrolyte-electrode interface due to the interaction of ions in the electrolyte solution and charges in the electrode.

Figure 7:
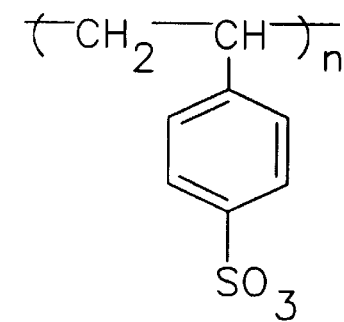
FIG. 7 depicts the proposed structure of PP-PSS films with three types of PSS chains (Adapted from Prezyna, et al., *Macromolecules*, 24:5283–5287, 1991).
Figure 7:
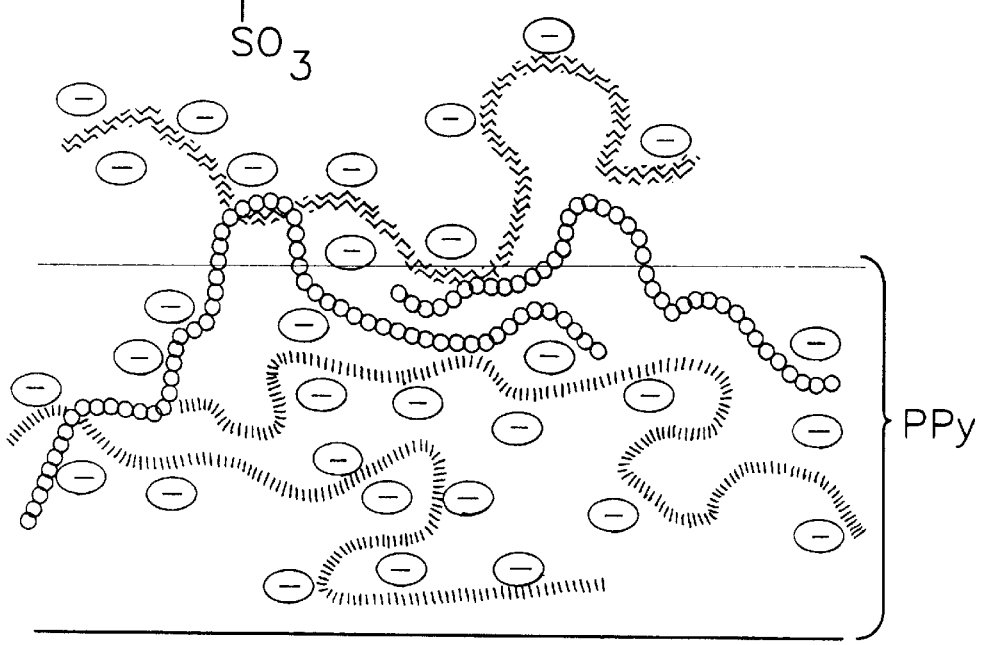

The presence of the negative sulfonate groups at the PPy/PSS surface is supported by previous work by Prezyna et al. (Prezyna et al., *Macromolecules*, 1991, 24, 5283). They suggested the presence of three types of PSS chains in the polypyrrole/PSS films (FIG. 7). The first (Type 1) includes well entangled chains contained in the bulk of the oxidized PPy film and are used relatively efficiently in doping. Type 2 PSS anions are thought to exist near the film surface, with only a portion of the chains acting as a dopant and the remainder are neutralized by Na cations in the electrolyte. Type 3 PSS chains are only slightly utilized as dopant chains and are loosely held by physical interactions at the film surface. It is the latter two types that have sulfonate moieties available for surface complexation and contribute to changing the nature of the polypyrrole/PSS surface. Thus, it can be concluded that the polypyrrole surface is rich in excess negatively charged sulfonate groups.

Figure 8:
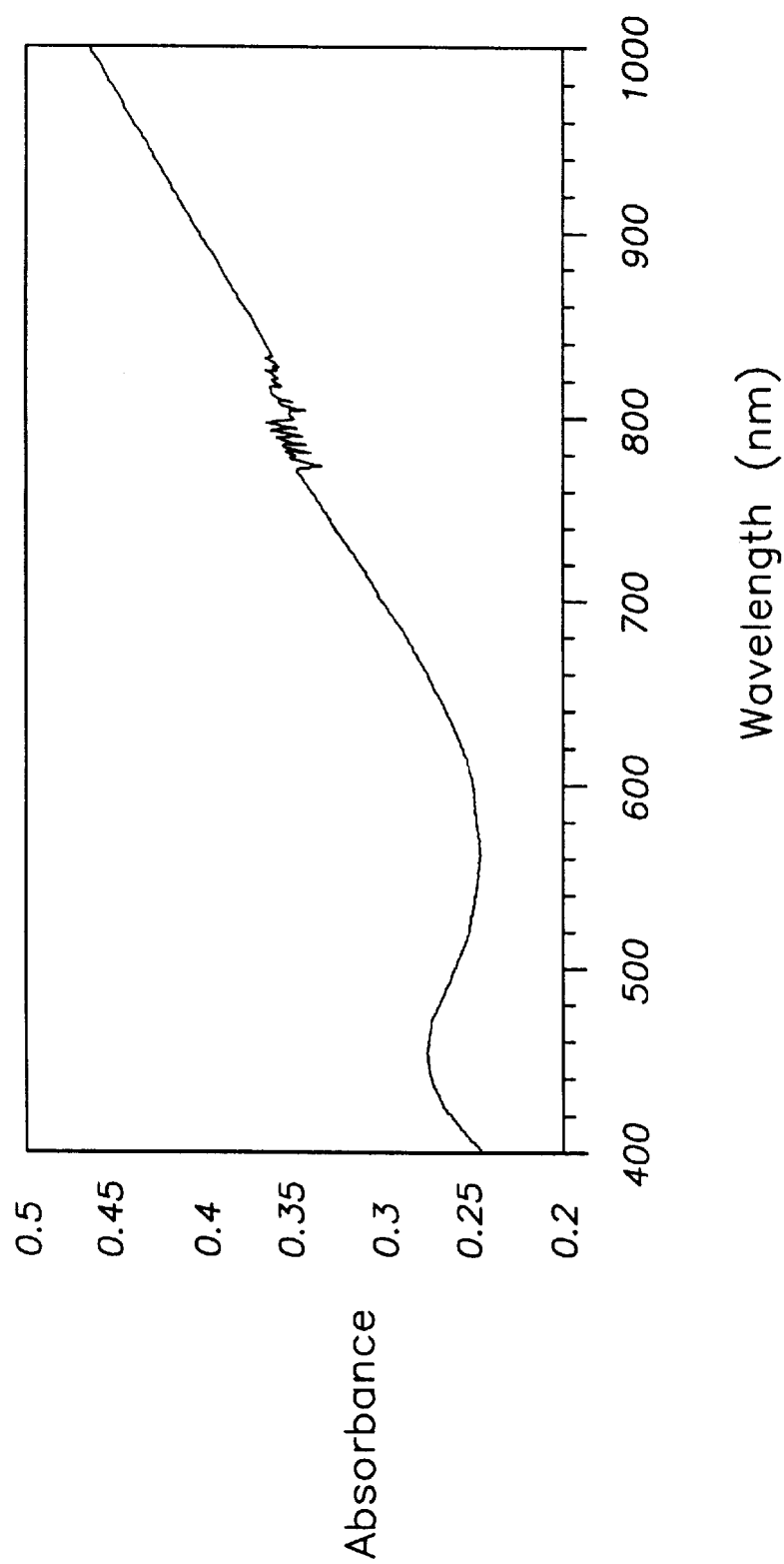
FIG. 8 depicts the UV/VIS absorption spectrum for a PP-PSS 0.1 $\mu$m thick film.

The optical properties of PPy films were determined by UV/VIS spectroscopy (FIG. 8). The absorption spectrum shows a broad peak at 450 nm, which has been attributed to the oxidized polymer (Street, G. B., "Polypyrrole: From powders to plastics", in Handbook of Conducting Polymers, T. A. Skotheim, Ed., 1986: New York, 265). The broad peak around 800 nm is believed to be due to the presence of bipolarons in the oxidized polymer (Scott et al., *Synth. Met.*, 1984, 9, 165; Blackwood et al., *J. Phys. Chem.*, 1991, 95, 493).

Figure 9:
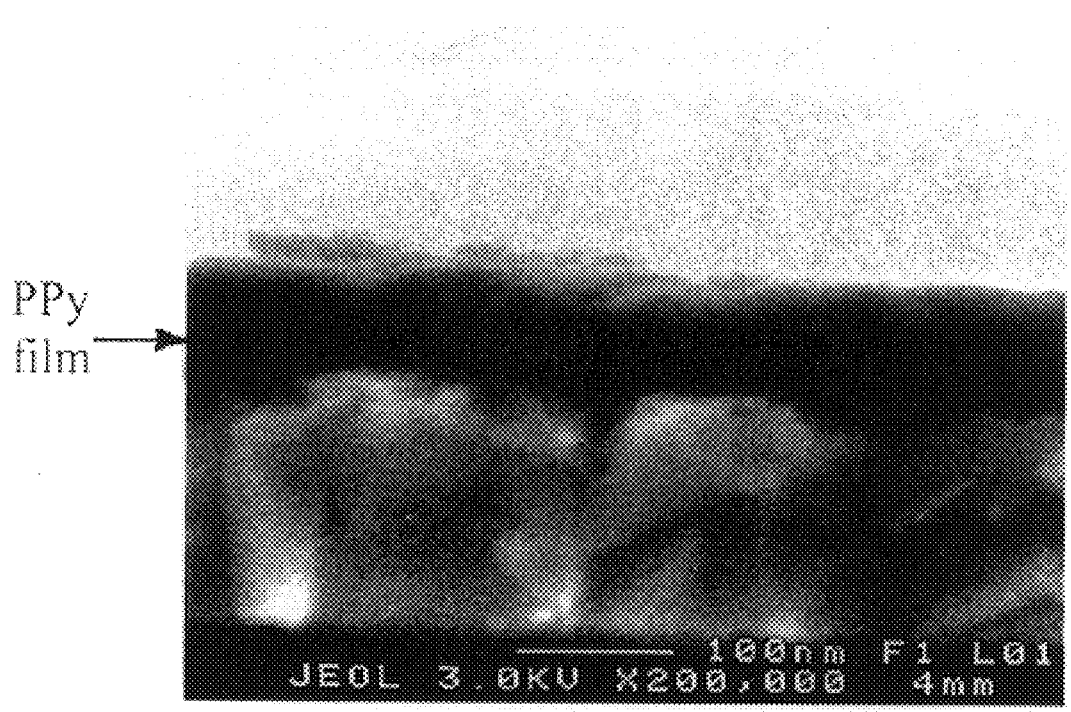
FIG. 9 depicts the Scanning Electron Micrograph of a cross section of a PPy film.
Figure 10:
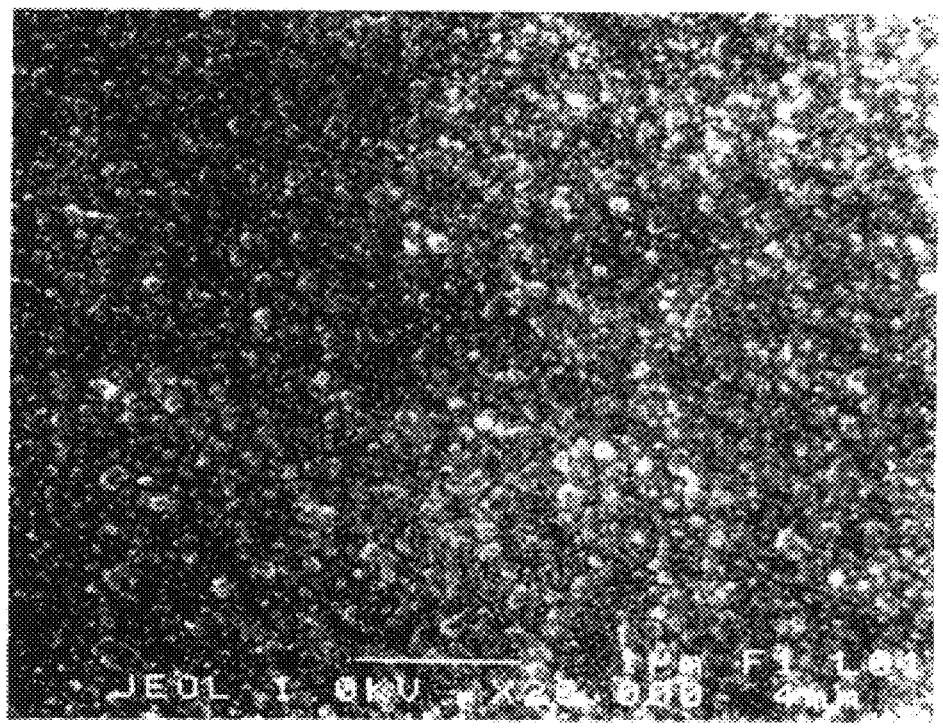
FIG. 10 depicts the Scanning Electron Micrograph of a surface of a PPy thin film.

SEM was used to analyze the surface and cross section of the Ppy thin films. The thickness of the films, which was estimated by the amount of charge passed during the electrodeposition process, was 0.1 um. This thickness was found to correlate well with the observed thickness of 0.08–0.1 um, using SEM analysis of the cross section (FIG. 9). The SEM of the surface of the PPy film is shown in FIG. 10. At an accelerating voltage of 1 kV, the films were seen to have a rough morphology, with numerous nodules. Since a constant potential electrochemical method was used, the growth is by instantaneous nucleation followed by nodular growth on the initially nucleated sites. This leads to the observed rough morphology, which is consistent with previous studies in which polypyrrole was electrochemically synthesized at constant potential in aqueous media (Asavapiriyanont et al., *J. Electroanal. Chem.*, 1984, 117, 245; Ko et al., *J. Electrochem. Soc.*, 1990, 137, 905). Furthermore, the nodular structure of the PPy/PSS films were also observed by Yang et al. (Yang et al., *Langmuir*, 1991, 7, 556). They investigated the individual conformations of the PSS chains in the films by means of Scanning Tunnelling Microscopy (STM). The PSS anions were found to be coated on the outside of the helical polypyrrole chains instead of being incorporated fully within the helical structure. This structural arrangement could be a further explanation for the presence of sulfonate moieties at the polypyrrole surface as observed by XPS, and also provide additional evidence for the model proposed by Prezyna (FIG. 7).

Additionally, the conductivity of the polypyrrole films was evaluated. Based on a rough estimate of the resistance, the conductivity was found to be in the order of 8.5 to 12 S/cm. The value confirmed that the polypyrrole was in the oxidized state. However, since thin films are being employed for the purposes of optically transparent substrates for cell culture studies, the conductivity is compromised. Conductivity in the order of 100 S/cm can be obtained with thicker films using the electrochemical synthesis method (Diaz et al., Bargon, J. "Electrochemical Synthesis of Conducting Polymers", in Handbook of Conducting Polymers, T. A. Skotheim, Ed., 1986: New York, 81).

The XPS results obtained suggest the presence of negatively charged sulfonate groups at the surface of the films. It is believed that these sulfonate moieties play a key role in the cellular interactions between the surface of the cells directly attached to it. SEM studies confirmed the rough nodular morphology of PPy films consistent with past observations. Conductivity and UV/VIS spectroscopy data established the existence of polypyrrole in its oxidized state.

Figure 11:
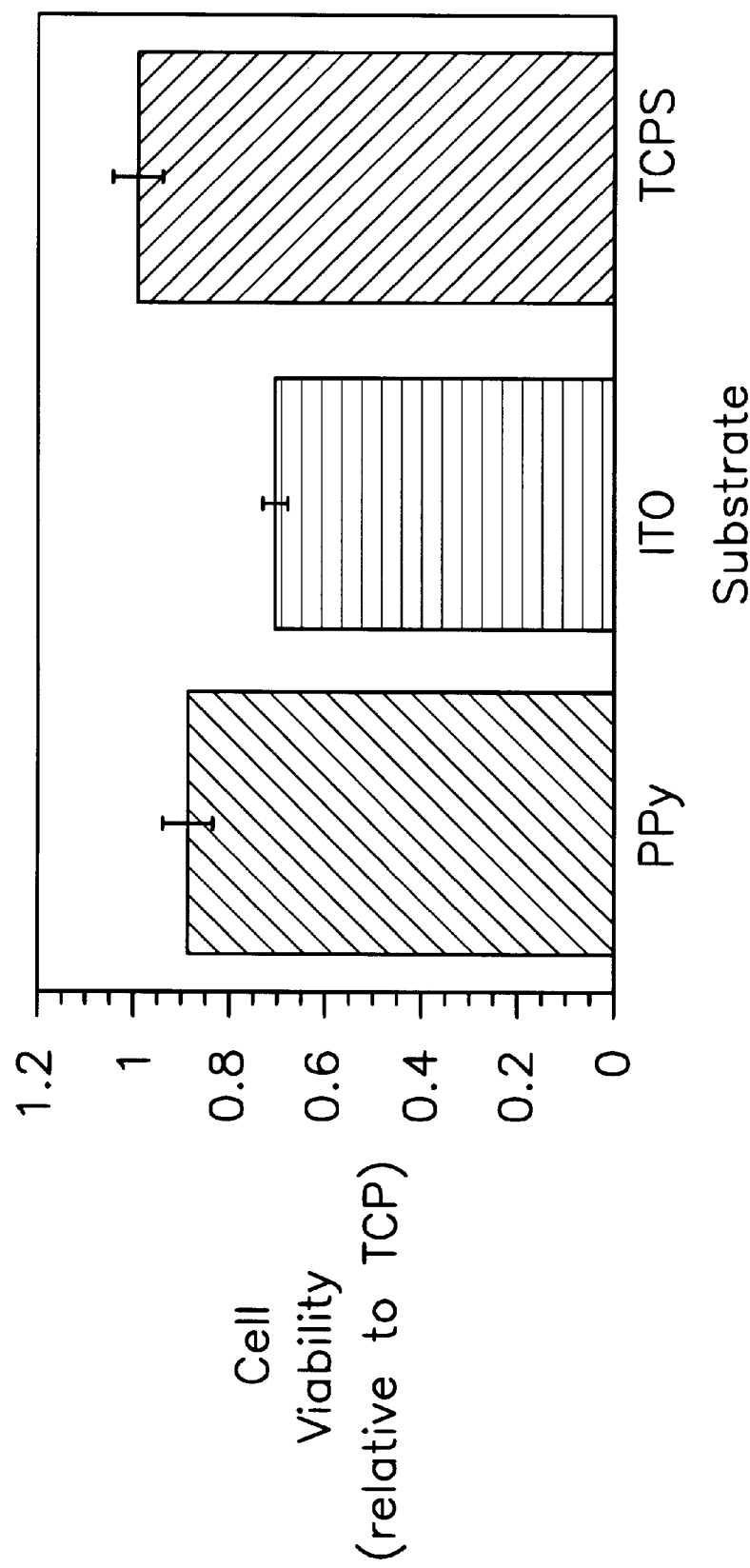
FIG. 11 depicts the cell viability of BMSC normalzed to tissue culture polystyrene and expressed as the mean +/−SD of three experiments for which the samples were tested in duplicate.

After polypyrrole had been synthesized and characterized, the ability of cells, specifically bone marrow stromal cells in this case, to attach to polypyrrole and proliferate was examined. Towards this end, bone marrow stromal cells grown on thin polypyrrole films, ITO and TCPS were tested for cell viability (FIG. 11). BMSC growth was supported on polypyrrole films indicating that polypyrrole is not toxic to them. In contrast, at 48 hours, cell viability was significantly lower on the ITO controls, indicating that the presence of the polypyrrole substrate enhanced cell attachment and proliferation.

Figure 12:
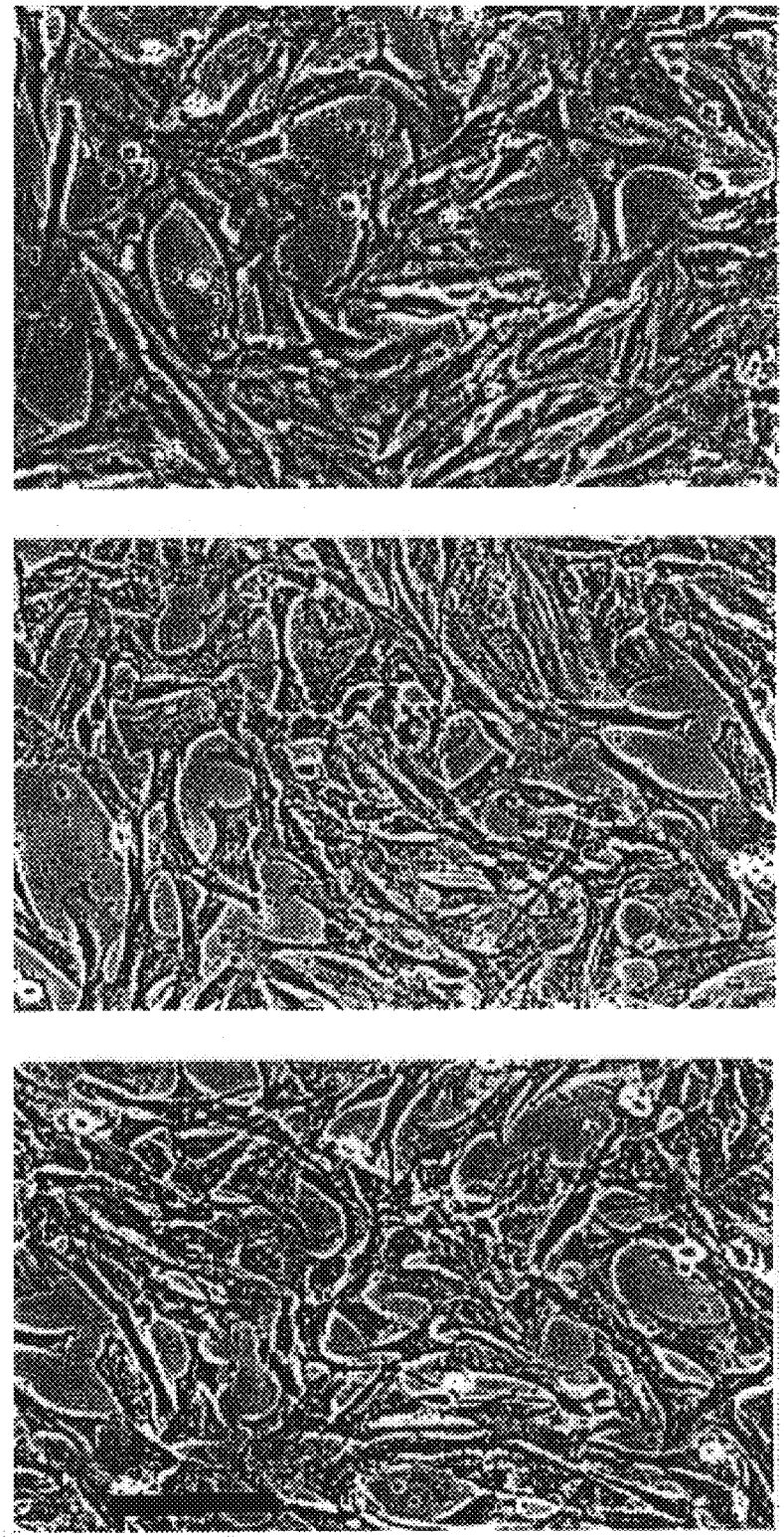
FIG. 12 depicts photomicrographs of BMSC on PPy film (top); TCPS (middle); ITO (bottom) after 48 hr incubation (bar=100 $\mu$m).
Figure 13:
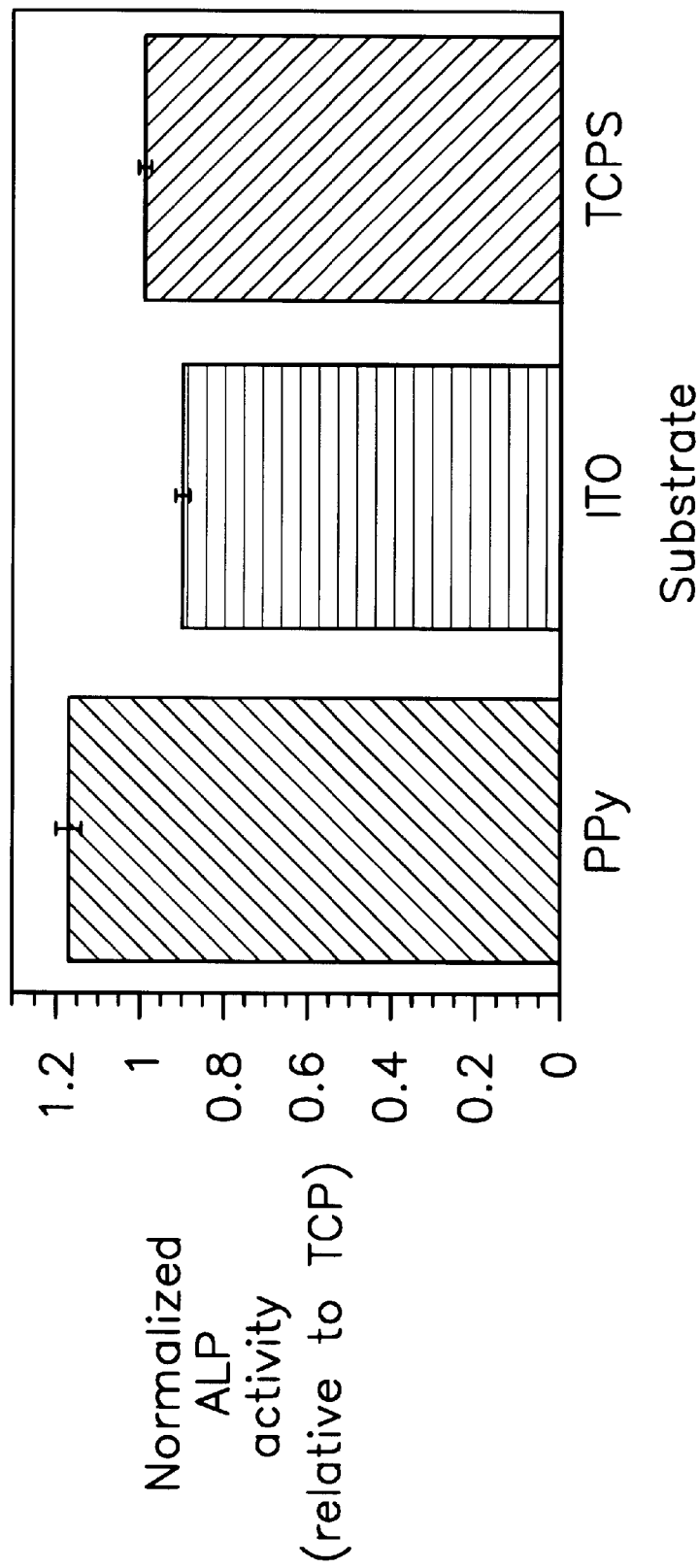
FIG. 13 depicts alkaline phosphatase activity of BMSC normalized on cell number (from MTT assay) relative to tissue culture polystyrene and expressed as the mean +/−SD of three experiments for which the samples were tested in duplicate.

Phase-contrast optical micrographs of BMSC cultured for 48 hours are shown in FIG. 12. It can be seen that the BMSC attach and spread equally well on all three substrates tested: PPy, ITO and TCPS. The cell morphologies seen on PPy are characteristic of those typicaly seen in TCPS Petri dishes.

Alkaline phosphatase (ALP) activity, a marker for BMSC differentiation towards the osteoblast phenotype, was found to be significantly higher for cells grown on PPy (FIG. 12). The activities for each of the substrates are normalized to the corresponding cell numbers obtained from the MTT assay and are represented relative to the TCPS control. It appears that the excess negative charges on the PPy surface, due to the incorporation of the poly(styrenesulfonate) dopant, could be encouraging an increased adsorption of certain matrix proteins that is favorable for the differentiation of the BMSC. The precise mechanism of this observed behavior is still unclear.

It has been shown that the nature of the charged substrate affects the migratory morphology of osteoblasts via the intermediation of specifically adsorbed proteins. For negatively charged substrata, it was shown that the ventral cell membrane was readily visible with only focal areas of close contact with the substratum, in contrast to positively charged substrata where the cell membrane was not distinguishable by transmission electron microscopy. It has been hypothesized that the space between either the osteoblasts or the osteoblast-like cells and negatively charged substrata could allow secretion of extracellular matrix (ECM) directly onto the substratum surface. It is desirable that there be close apposition of bone matrix with the biomaterial, and this is best achieved with ECM laid directly onto the surface. Hence, negatively charged substrata such as polypyrrole with the dopant ion PSS, or other electroactive materials, would be ideally suited to fulfill this objective.

Osteogenesis and formation of dense connective tissue has also been demonstrated by employing negatively charged Sephadex beads when implanted into cranial or mandibular defects in young adult rats (Krukowski et al., *Oral Maxillofac. Surg.*, 1990, 48, 468). The mechanism by which the charged beads fostered the osteogenic response is not well understood. Our in vitro observations with polypyrrole's negatively charged surface interactions with BMSC suggest tha the cells may be undergoing differentiation towards the osteoblast phenotype. A similar phenomenon as observed in vivo could also be occurring in vitro in promoting osteogenesis with negatively charged substrata.

In addition, the ability of cells grown on polypyrrole versus cells grown on tissue culture polystyrene to be induced to differentiate along the osteoblast lineage by glucocorticoids was examined. Glucocorticoids are steroid hormones that can regulate gene expression in differentiating cells and in inducing the affinity of the glucocorticoid receptors found in cells (Cutroneo, K. R., Sterling, K. M., Shull, S., "Steroid Hormone Regulation of Extracellular Proteins", in Regulation of Matrix Accumulation, R. P Mecham, Ed., 1986, Academic Press: New York, 119). Dexamethasone, a synthetic glucocorticoid, has been shown to induce the osteoblast phenotype and bone formation with stromal cells in vitro (Maniatopoulos et al., *Cell Tissue Res.*, 1988, 254, 317). Numerous studies with dexamethasone in marrow derived stromal cell culture have shown that an increase in alkaline phosphatase (ALP) activity occurs with the addition of the glucocorticoid (Cheng et al., *J. Cell. Biochem.*, 1996, 61, 182; Locklin et al., *Clin. Orthop. Rel. Res.*, 1995, 313, 27; Shalhoub et al., *J. Cell. Biochem.*, 1992, 50, 425; Malaval et al., *J. Cell. Phys.*, 1994, 158, 555; Leboy et al., *J. Cell. Physiol.*, 1991, 146, 370; Kasugai et al., *J. Cell Physiol.*, 1991, 147, 111; Thomson et al., *J. Bone Miner. Res.*, 1993, 8, 1173). The precise role of the steroid in modulating the metabolism and biological activity is not completely understood and is subject to investigation.

The typical "cocktail" of stimulants added to the culture to induce osteogenesis consists of dexamethasone, ascorbic acid, and β-glycerophosphate. Ascorbic acid is required for the synthesis of collagen and for osteogenesis in vitro. Furthermore, Anderson et al. (Anderson et al., In vitro, 1984, 20, 837) have demonstrated that ascorbic acid regulates ATPase and ALP activities and protein synthesis in cultures of osteoblast-like cells. The organic phosphate, b-glycerophosphate, has often been used in vitro as a potential source of phosphate ions (Bellows et al., *Calcif. Tissue Int.*, 1986, 38, 143; Tenenbaum et al., *Calcif. Tissue Int.*, 1982, 34, 76; Gehron-Robey et al., *Calcif. Tissue Int.*, 1985, 37, 453).

Figure 14:
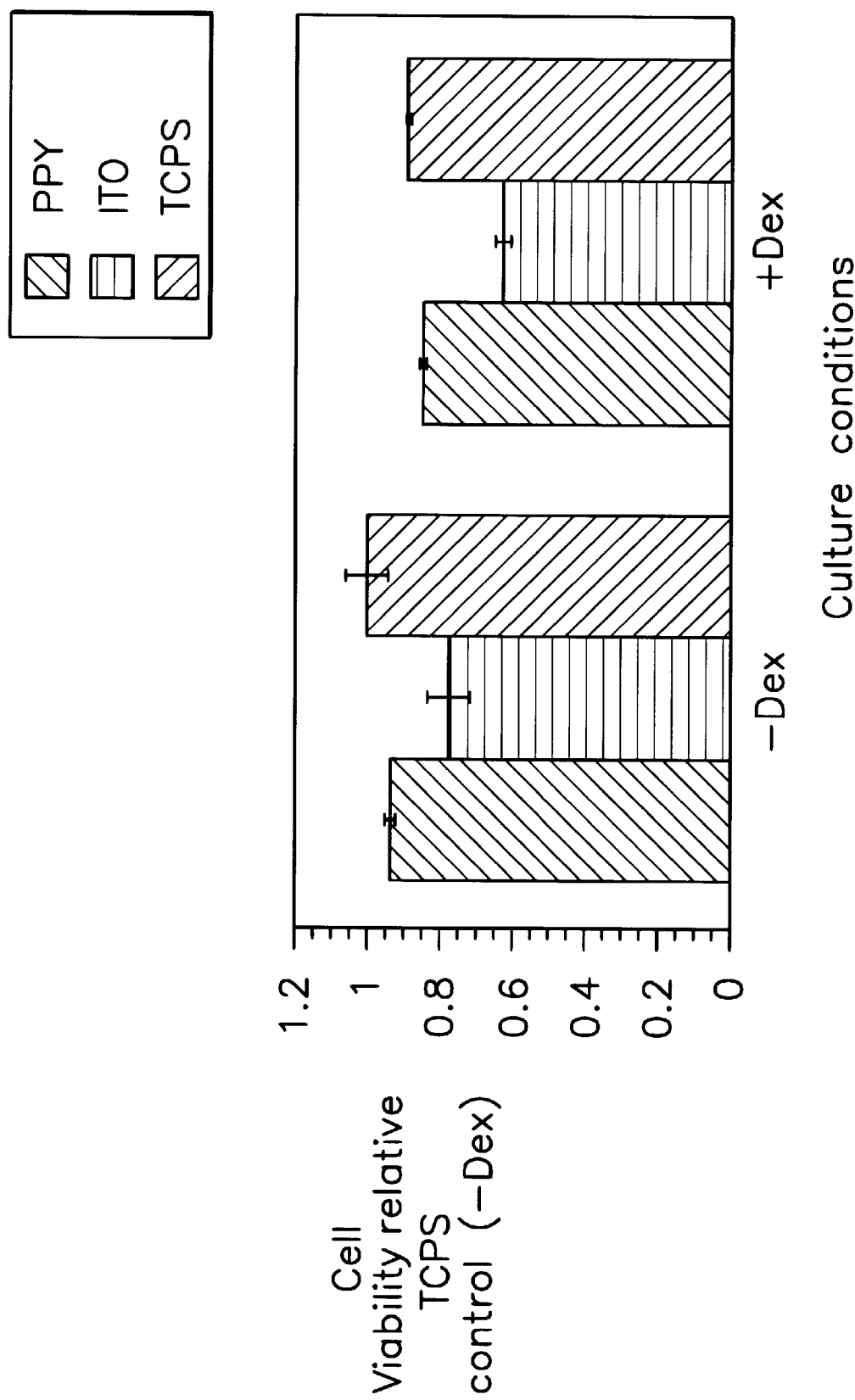
FIG. 14 depicts the cell viability of BMSC normalized to tissue culture polystyrene control without dexamethasone and expressed as the mean +/−SD of three experiments for which the samples were tested in duplicate.
Figure 15:
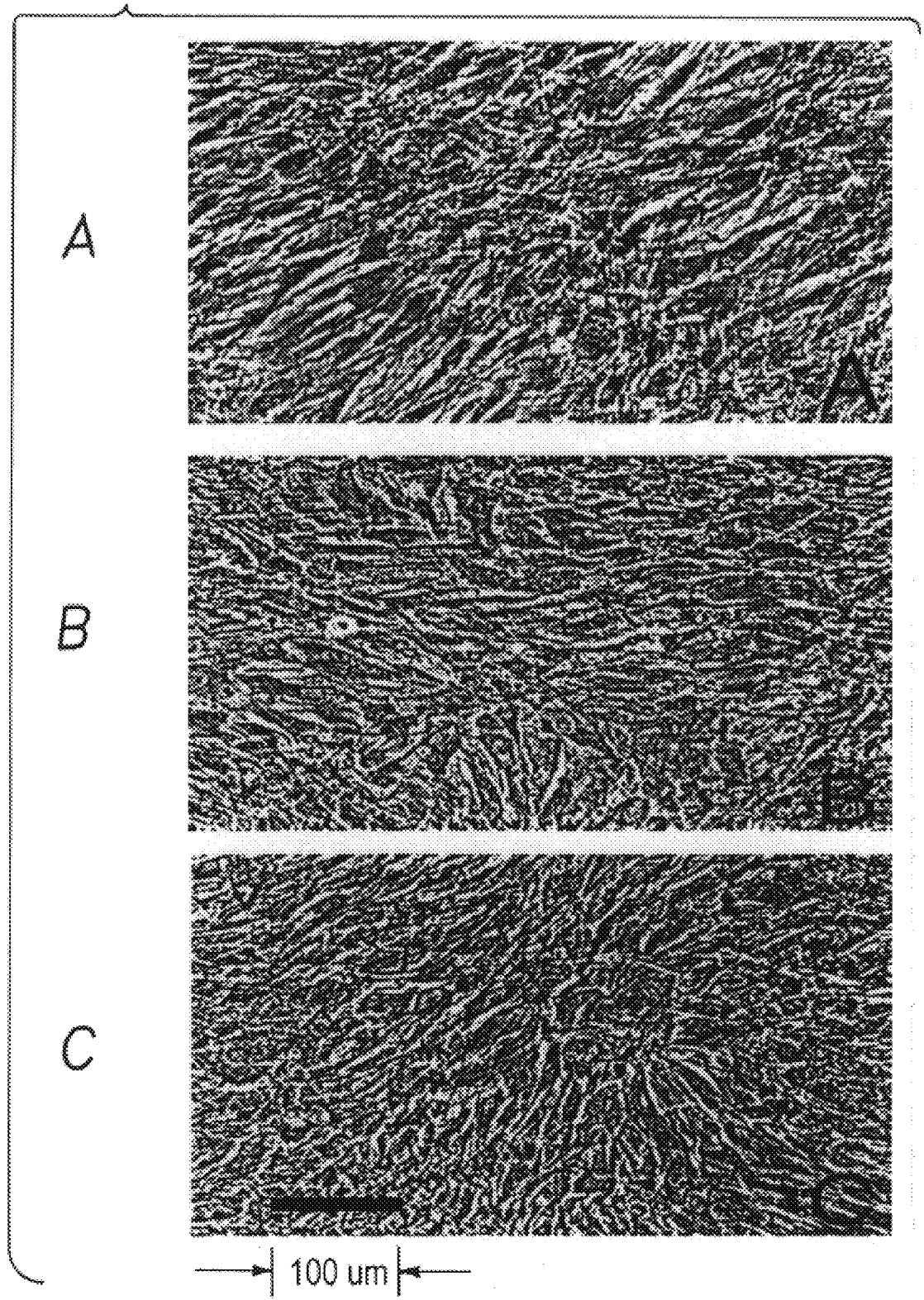
FIG. 15 depicts photomicrographs of dexamethasone supplemented cultures on PPy (A); TCPS (B); ITO (C) after 48 hr dex medium (bar=100 $\mu$m).

The cell viabilty of dexamethasone supplemented cultures on PPy and ITO were compared relative to TCPS controls (FIG. 14). The proliferation of cells was moderately reduced for all cultures in the presence of dexamethasone. The observed behavior is consistent with previous data (Cutroneo, K. R., Sterling, K. M., Shull, S., "Steroid Hormone Regulation of Extracellular Proteins", in Regulation of Matrix Accumulation, R. P. Mecham, Ed., 1986, Academic Press: New York, 119). Micrographs (FIG. 15) of the cultures on each of the substrates demonstrate the typical cuboidal shape of the cells on addition of dexamethasone.

Figure 16:
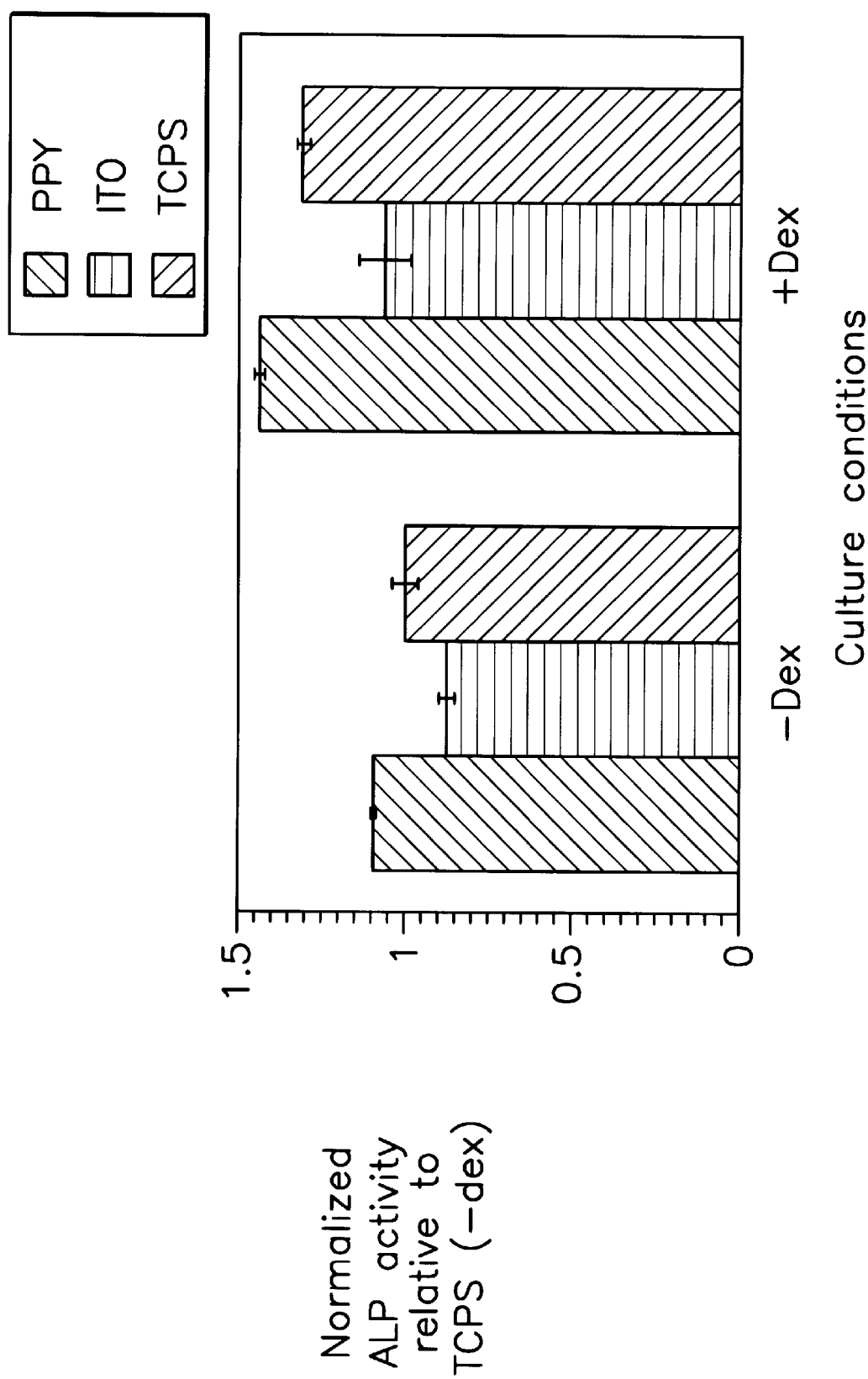
FIG. 16 depicts alkaline phosphatase activity of BMSC normalized on cell number (from MTT assay) relative to tissue culture polystyrene without dexamethazone and expressed as the mean +/−SD of three experiments for which the samples were tested in duplicate.

ALP activity was stimulated by dexamethasone on all three substrates (FIG. 16). However, the expression of the enzyme was significantly higher for PPy ($P<0.01$) relative to TCPS controls. Thus, PPy appears to be promoting osteogenesis to the osteoblast phenotype to a greater extent, relative to TCPS, in the presence of the glucocorticoid, dexamethasone. ALP activity is expected to be enhanced with dexamethasone from previous studies with BMSC cultures (Cheng et al., *Cell Biochem.*, 1996, 61, 182; Locklin et al., *Clin. Orthop. Rel. Res.*, 1995, 313, 27; Malaval et al., *J. Cell. Phys.*, 1994, 158, 555; Kasugai et al., *J. Cell. Physiol.*, 1991, 147, 111). However, the enhanced expression of PPy, in contrast to that on TCPS, could again be a result of the interactions between the polypyrrole surface chemistry and adsorption of certain proteins on the surface, which could be triggering the ALP activity via the regulation of the glucocorticoid.

The evaluation of PPy as a medium for the electrical stimulation of BMSC was then explored (Korenstein et al., *Biochem. Biophys. Acta.*, 1984, 803, 302; Ozawa et al., *J. Cell. Physiol.*, 1989, 138, 477; Brighton et al., *Clin. Orthop.*, 1992, 285, 255; Gupta, R., Naranja, R. J., Levit, C. L., Brighton, C. T. "The Biochemical Pathway of Capacitively Coupled Electric Field Stimulation of Osteoblast-Like Cells", in Proceedings of the 14th Annual Meeting of the Society for Physical Regulation in Biology and Medicine, 1994, Washington, D.C.). Numerous researchers have studied the effect of electrical stimulation in vitro on bone cells. However, there are no reports of bone cells cultured directly on a substrate that was electrically conductive. The use of PPy is thus a novel approach in applying electrical stimulation to bone cells. Through this arrangement, it is hypothesized that electrical coupling between the cells nad the electrode will be enhanced since the cells are directly attached to the PPy electrode. Furthermore, the enhanced alkaline phosphatase activity of BMSC from the base line and glucocorticoid studies have indicated that the nature of the PPy surface, due to the incorporation of the poly (styrenesulfonate)dopant anion, could be playing a role in the protein adsorption or other unknown cellular processes.

Figure 17:
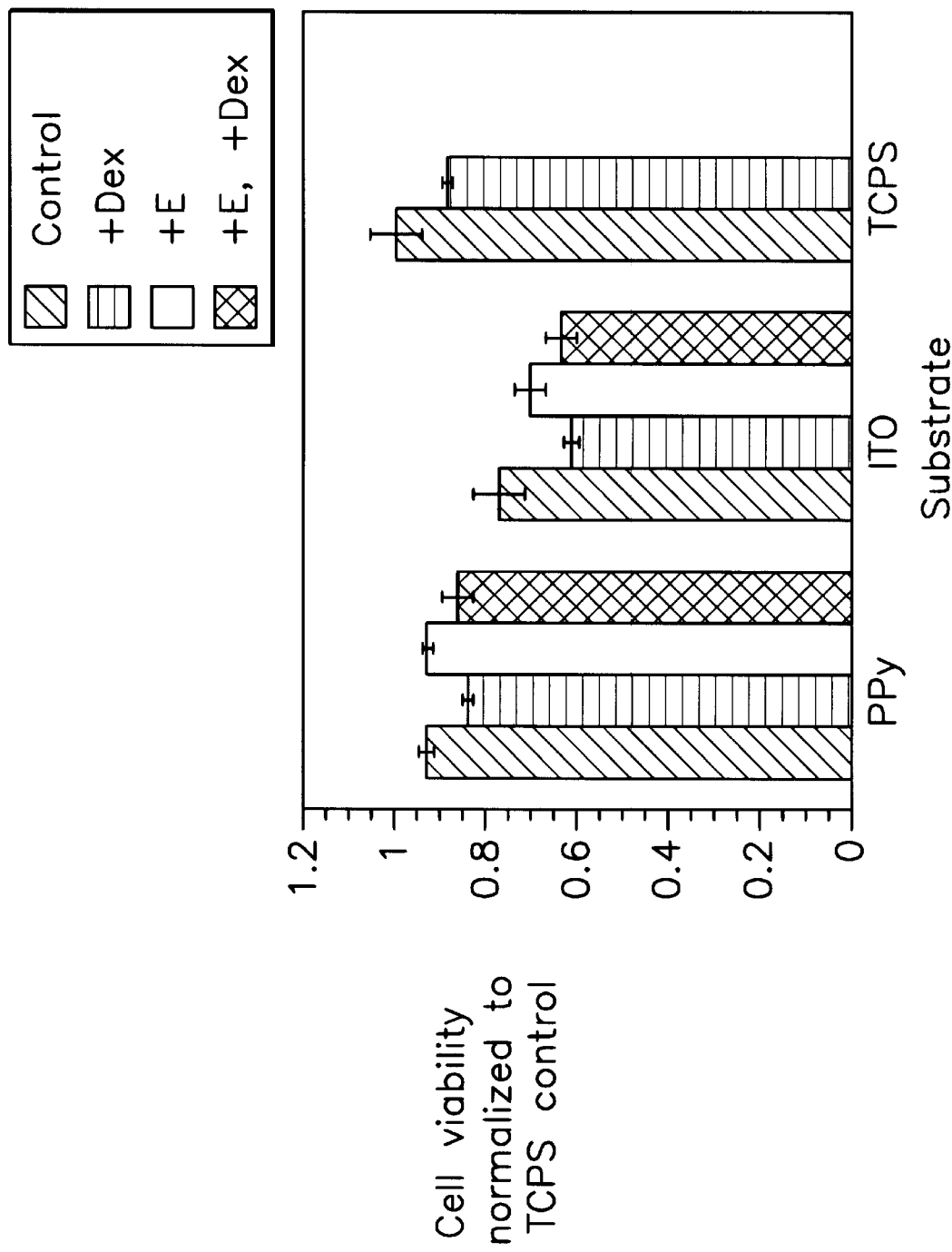
FIG. 17 depicts cell viability of BMSC normalized to tissue culture polystyrene control without dexamethasone and expressed as the mean +/−SD of three experiments for which the samples were tested in duplicate.

As a result of these studies, it was determined that cell viability, normalized to TCPS, was not affected significantly upon electrical stimulation on both the PPy and ITO substrates in the (+E) and dexamethasone supplemented (+E, +Dex) cultures (FIG. 17). However, relative to PPy, the cell viability of the cultures on ITO was significantly lower for two of the four conditions studied: BMSC grown on ITO controls with dexamethasone (+Dex) only, and BMSC grown on ITO with dexamethasone and electrical stimulation (+E, +Dex). The mechanism for the reduced cell number on ITO glass is not understood but supports the hypothesis that the surface of the polypyrrole interacts with charged matrix proteins, both in the presence and absence of electrical stimulation, to support cell growth and attachment. Since the application of the constant potential at 100 mV for 1 hour did not significantly affect cell viability for both dexamethasone and control cultures on polypyrrole, it appears that this stimulus does not initiate cell death during the stimulation and 24 hour post stimulation periods.

Figure 18:
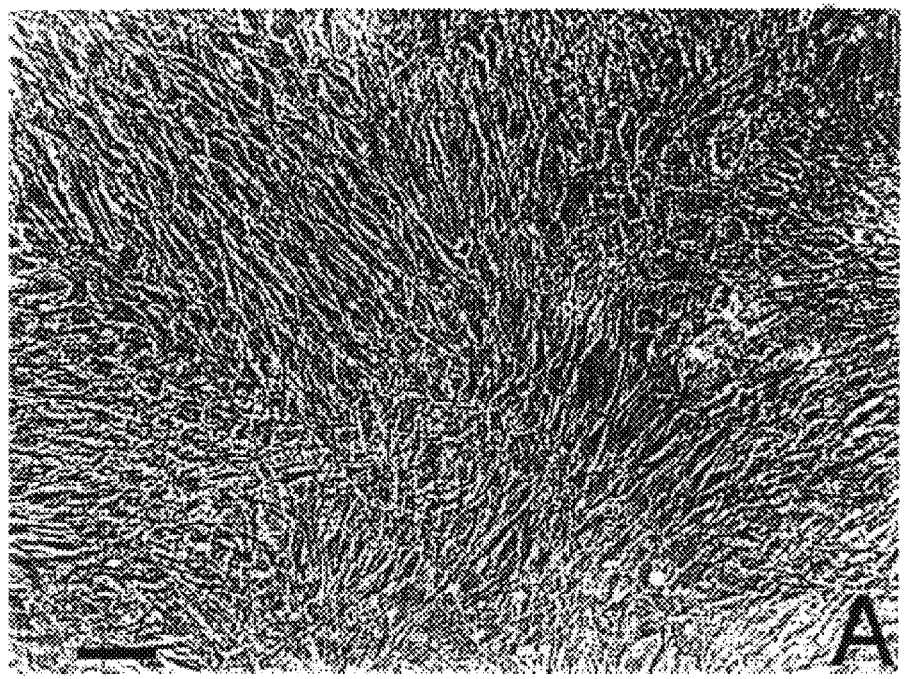
FIG. 18 depicts photomicrographs of BMSC 24 hr after electrical stimulation when cultured on PPy (A) and ITO in (+E, +dex) condition (bar=100 $\mu$m).
Figure 18:
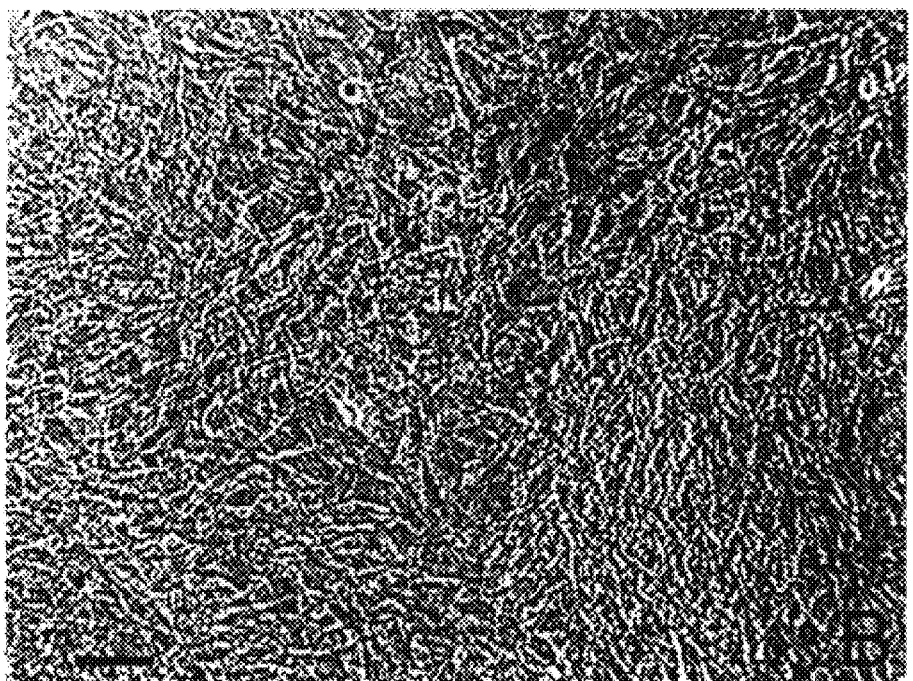

Phase contrast micrographs of BMSC cultured on PPy and ITO, in the presence of dexamethasone and exposed to electrical stimulation are shown in FIG. 18. During this short stimulation period, it is not surprising to see that there was no change in morphology relative to control cultures without the electrical stimulation. The cuboidal shape of the cells as seen in the dexamethasone cultures is still maintained upon electrical stimulation.

Figure 19:
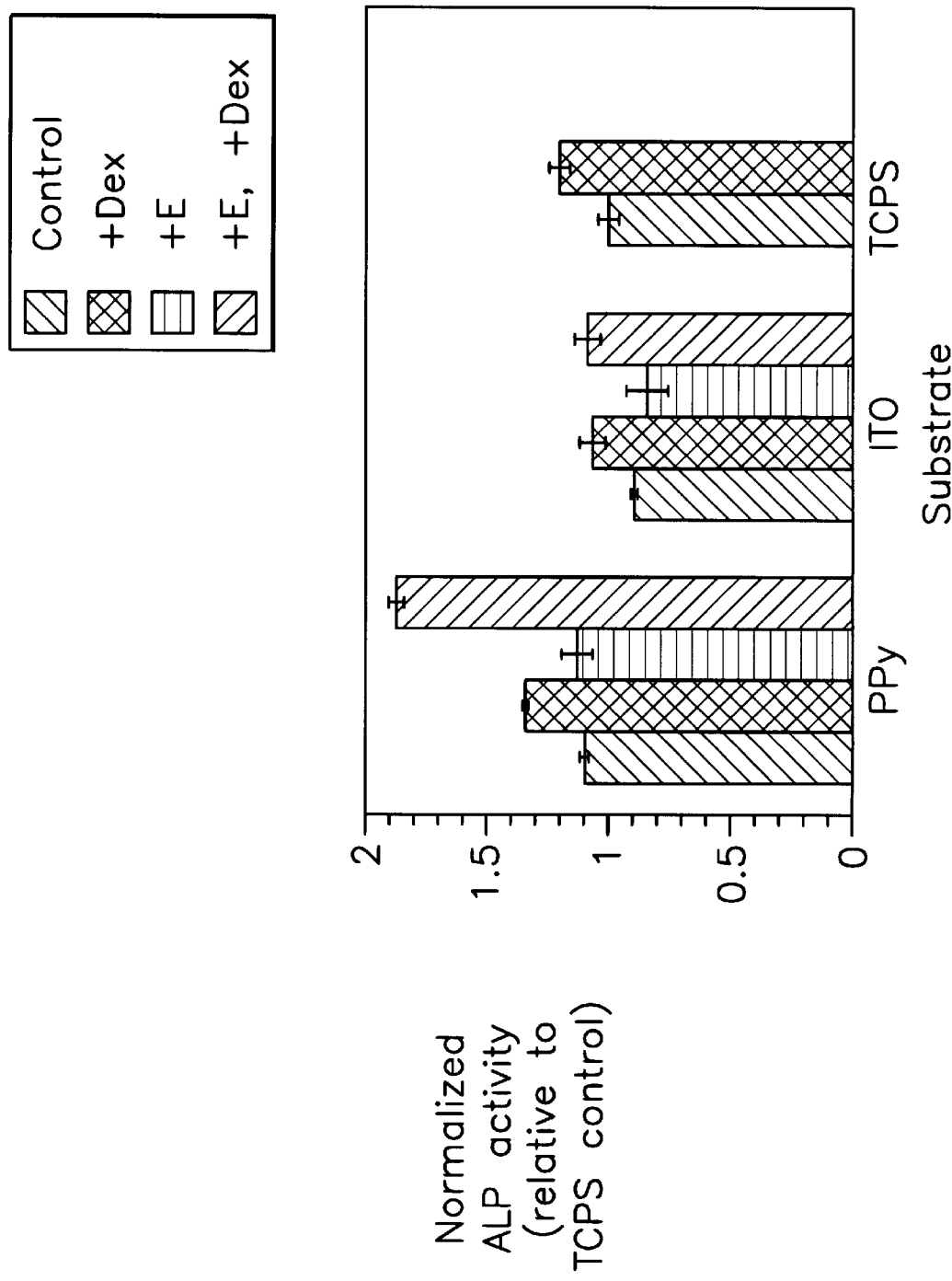
FIG. 19 depicts alkaline phosphatase activity of BMSC normalized on cell number (from MTT assay) relative to tissue culture polystyrene without dexamethazone and expressed as the mean +/−SD of three experiments for which the samples were tested in duplicate.
Figure 20:
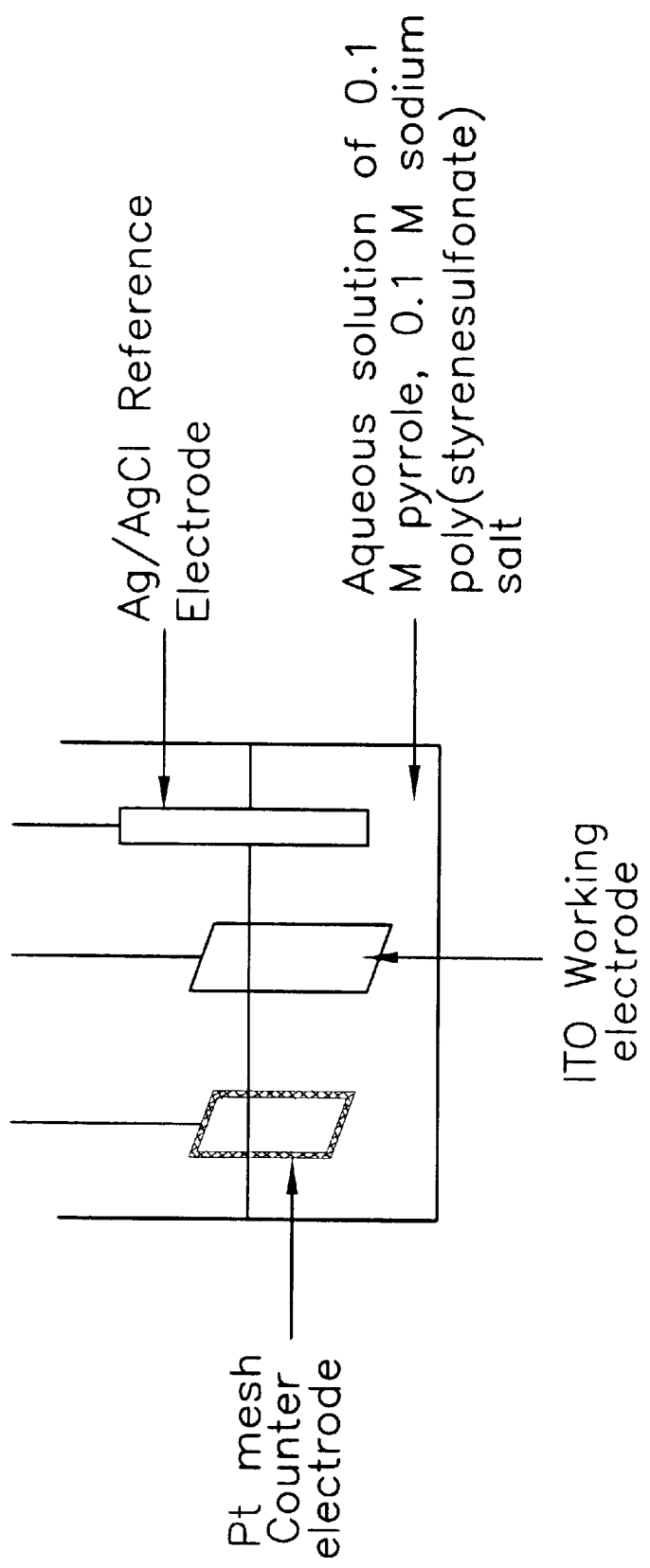
FIG. 20 depicts the setup for the electrodeposition of PPy thin films onto ITO working electrode.

Although no dramatic changes were observed in the cell morphology of BMSC cultured on PPy in the (+E, +Dex) condition, the ALP activity was found to increase by 40% (P<0.01) relative to PPy control cultures without electrical stimulation (+Dex) (FIG. 19). Since the cell viability was relatively unaffected by the application of the stimulus, these observations could be a result of an increase in the number of marrow stromal cells expressing ALP and/or an increase in the amount of ALP expressed per cell. In contrast, ALP activity remained unchanged for electrically stimulated cultures without dexamethasone (+E) versus PPy cultures without both electrical stimulation and dexamethasone (Control). The interaction of the cells with the PPy substrate in the presence of dexarnethasone during the electrical stimulus appears to be triggering a mechanism to markedly differentiate the cell along the osteoblastic phenotype. It appears that the presence of the glucocorticoid is essential during the stimulation period to observe this significant increase at the chosen constant potential level of 100 mV for 1 hour.

However, the nature of the surface was also demonstrated to be crucial in determining cellular behavior since ALP activity was significantly increased (+56%, P<0.01) in PPy cultures in the presence of electrical stimulation and dexamethasone (+E, +Dex) relative to ITO cultures under the same conditions. Even though the ITO substrates are highly conductive (in the order of 800 S/cm as reported by manufacturer), the mere application of a steady potential thorough the electrode was not capable of inducing osteogenic differentiation of the BMSC. Thus, the interaction of the PPy surface and application of electrical stimulation through the film itself was necessary to obtain the observed increase in ALP activity.

Several hypotheses can be put forth to explain the effect of PPy on BMSC during electrical stimulation. As suggested above, the excess negatively charged sulfonate groups on the PPy surface could be playing a role in changing the conformation of certain adsorbed proteins upon the application of electrical stimulation. Furthermore, it appears that there is a coupled effect of dexamethasone and electrical stimulation in enhancing ALP activity on PPy, as the effect was not observed upon application of electrical stimulation (+E) alone. Thus, the interaction of PPy and proteins involved in the dexamethasone regulatory pathway of the alkaline phosphatase gene expression, could also be playing an important role. The mechanism by which dexamethasone induces alkaline phosphatase activity is not fully understood. However, studies have suggested that either a mediator protein is involved in the action of dexamethasone on alkaline phosphatase at a pretranslational level (Green et al., *Eur. J. Biochem.*, 1990, 188, 147) or that the increase in alkaline phosphatase activity in dexarnethasone cultures is via the de novo syntheisis of the ALP enzyme itself (Majeska et al., *Endocrinology*, 1985, 116, 170) It may be possible that the interaction between an adsorbed protein layer on the polypyrrole surface and the "mediator" protein could be leading to certain conformational changes that result in the elevated activity of ALP.

The role of $Ca^{2+}$ ions in electrical stimulation could also be important in determining the differentiation level of BMSC (Ozawa et al., *J. Cell. Physiol.*, 1989, 138, 477). Voltage grated calcium channels exist in the membranes of bone marrow cells and osteoblasts in which the ion transport is mediated by electrical stimulation. Ozawa et al. showed that electrical fields stimulate the DNA synthesis of MC3T3-E1 (mouse osteoblast-like cells) by a mechanism involving calcium ions. More recently, it has been shown that capacitively coupled electrical stimulation of these cells induces an elevation in the level of TGF-β, an important growth factor in the formation of bone and cartilage (Zhuang, H., Wang, W., Seldes, R. M., Tahernia, A. D., Fan, H., Brighton, C. T., "Electrical Stimulation Induces the Level of TGF-β1 MRNA in Osteoblastic Cells by a Mechanism Involving Calcium/Calmodulin Pathway", 1997, 237, 225. The mechanism is believed to involve a calcium/calmodulin pathway. Calmodulin is a ubiquitous intracellular calcium-binding protein that interacts with a wide range of enzymes. An increase in the concentration of cytosolic $Ca^{2+}$ leads to an activation of calmodulin, which is responsible for many calcium-mediated processes including proliferation and differentiation of cells. Thus, modulation of calcium transport thorough voltage grated channels, as a result of the electrical stimulation, could be mediating certain cellular differentiation pathways. Furthermore, calcium transport is also affected by dexamethasone. Publicover et al. (Publicover et al., *Calcif. Tiss. Int.*, 1994, 54, 649) have shown that low voltage-activated $Ca^{2+}$ channels are induced in rat bone marrow stromal cells by dexamethasone to exhibit osteoblast-like channel modulation. Since the coupling of dexamethasone and electrical stimulation together was necessary to increase the ALP activity in our system, it may be possible that the two calcium transport processes and associated cellular pathways could be interacting to augment the observed osteogenic differentiation.

Lastly, it can also be suggested that the negatively charged polypyrrole surface could be binding the positively charged $Ca^{2+}$ counterions during the electrical stimulation and thus triggering the activity of the alkaline phosphatase enzyme, possibly by means of a transmembrane protein or some other unknown mechanism. Furthermore, if the $Ca^{2+}$ ions are indeed bound to the negatively charged sulfonate groups, the polymer surface could be acting as a localized source of $Ca^{2+}$ ions near the cell surface.

EXPERIMENTALS

EXAMPLE 1

Polymer Synthesis and Characterization a. Chemicals and Materials:

Pyrrole and sulfonated polystyrene sodium salt (MW 70,000) were obtained from Aldrich (Milwaukee, Wis.). Activated alumina was purchased from Mallinckrodt (Chesterfield, Mo.). Indium tin oxide (ITO) conductive borosilicate glass (40/square, 50×25 mm) was obtained from Delta Technologies (Still Water, Minn.) and used as the electrochemical conductive surface for PP film deposition. Hexane, dichloromethane and methanol were purchased from EM science (Gibbstown, N.J.). A platinum gauze (99.9% Pt, 52 mesh, woven from 0.1 mm diameter wire) served as the counter electrode and was purchased from Aldrich Chemical Co. An Ag/AgCl electrode was purchased from Fisher Scientific (Pittsburgh, Pa.) and was used as the reference electrode. Ultrapure water was obtained from Millipore Milli-Q Reagent Water System (Bedford, Mass.).

b. Polymer Synthesis:

Pyrrole was passed though an activated alumina column, consisting of a standard 9" pasteur pipette plugged with glass wool and packed with activated alumina, until it became colorless. Indium tin oxide substrates were ultrasonically cleaned in hexane, methanol and dichloromethane sequentially for 5 min. each. A three electrode setup was used for the electrochemical synthesis of polypyrrole (PPy): the ITO glass acted as the working electrode, the platinum mesh as the counter electrode and the Ag/AgCl electrode as the reference (FIG. 19). The electrodeposition solution contained 0.1 M pyrrole and 0.1 M sodium salt of poly (styrenesulfonate) (PSS) and Milli-Q ultra pure water. The sodium salt of poly(styrenesulfonate) served as both the electrolyte and dopant. An EG & G Princeton Applied Research Potentiostat/Galvanostat Model 253A (Princeton, N.J.) was employed as the constant voltage source. PPy films (0.1–0.15 um) were deposited onto the ITO glass at a constant potential of 0.7 V versus the Ag/AgCl reference electrode. The film thickness was controlled by the passage of charge: a charge of 26.2 mC/cm$^2$ yields a PPy film of 0.1 um in thickness.

c. X-Ray Photoelectron Spectroscopy (XPS) Spectra were obtained using a Surface Science Laboratories X-100 spectrometer (Mountain View, Calif.) employing a monochromatized Al Ka (1486.7 eV) Xray source operated under a source chamber vacuum of ~1×10-9 torr. Core level spectra were taken at a take-off angle of 35 (measured with respect to the normal to the sample surface). Photoelectrons were analyzed by a hemispherical multichannel detector in fixed analyzer transmission mode. An electron flood gun (energy 5 eV) was used to compensate for charging during X ray Photoelectron Spectroscopy data acquisition. A nickel mesh in electrical contact with the spectrometer was placed approximately 1 mm over samples to assist the compensation. For all spectra, the X-ray spot size was 1000 um. Survey spectra were recorded over a binding energy range of 0 to 1000 eV using a pass energy of 300 eV. Surface chemical compositions were determined from peak-area ratios corrected with the appropriate experimentally determined sensitivity factors.

d. UV/VIS Spectroscopy:

UV/Visible spectroscopic data were obtained using a Cary SE UVVIS-NIR Spectrophotometer from Varian OSI (Melbourne, Australia). A dual beam system with a scan rate of 600 mn/min was employed.

e. Scanning Electron Microscopy (SEM):

A JEOL Scanning Microscope Model 6320 (Akishima, Japan) was used for surface and cross sectional analysis of the PPy thin films. Ppy samples were mounted on aluminum stubs using conductive tape to observe the surface. For the cross section of the film, the PPy sample on the ITO glass was cut finely using a diamond cutter. It was mounted in a vice with the interface of interest facing up. Photographs of the images were obtained using a Polaroid instant camera and Polaroid 55 positive negative film.

f. Conductivity:

Since the PPy films were grown on ITO (resistance of 40/sq reported by manufacturer), an estimate of the conductivity was made by measuring the resistance of the films with a Micronta multimeter. The probes of the multimeter were lightly touched onto the PPy film and the surface resistance was recorded. The surface conductivity, σ, the reciprocal of resistivity, ρ, was calculated from the cross-sectional, area (A) of the film and distance (L) between the multimeter probes as shown in equation X below:

$$\sigma = \left(\frac{1}{\rho}\right) = \left(\frac{L}{RA}\right)$$

EXAMPLE 2

Cell Culture-Base Line Studies a. Chemicals and Materials:

Dulbecco's Modified Eagle Medium (DMEM), fetal bovine serum (FBS), Dulbecco's phosphate buffered saline (PBS) without additives, penicillin, streptomycin, nonessential amino acids and trypsin were purchased from Gibco BRL (Grand Island, N.Y.). Recombinant Human fibroblast growth factor-2 was purchased from R & D systems (Minneapolis, Minn.). Tissue culture polystyrene Petri dishes were purchased from either Falcon (Becton Dickinson & Co., Franklin Lakes, N.J.) or Corning (Corning, N.Y.). MTT (3-[4,5-dimethylthiazol-2-yl]-2,5-diphenyltetrazolium bromide; Thiazolyl blue), a mitochondrial stain for cell viability was purchased from Sigma. Alkaline Phosphatase kits were purchased from Sigma.

Figure 21:
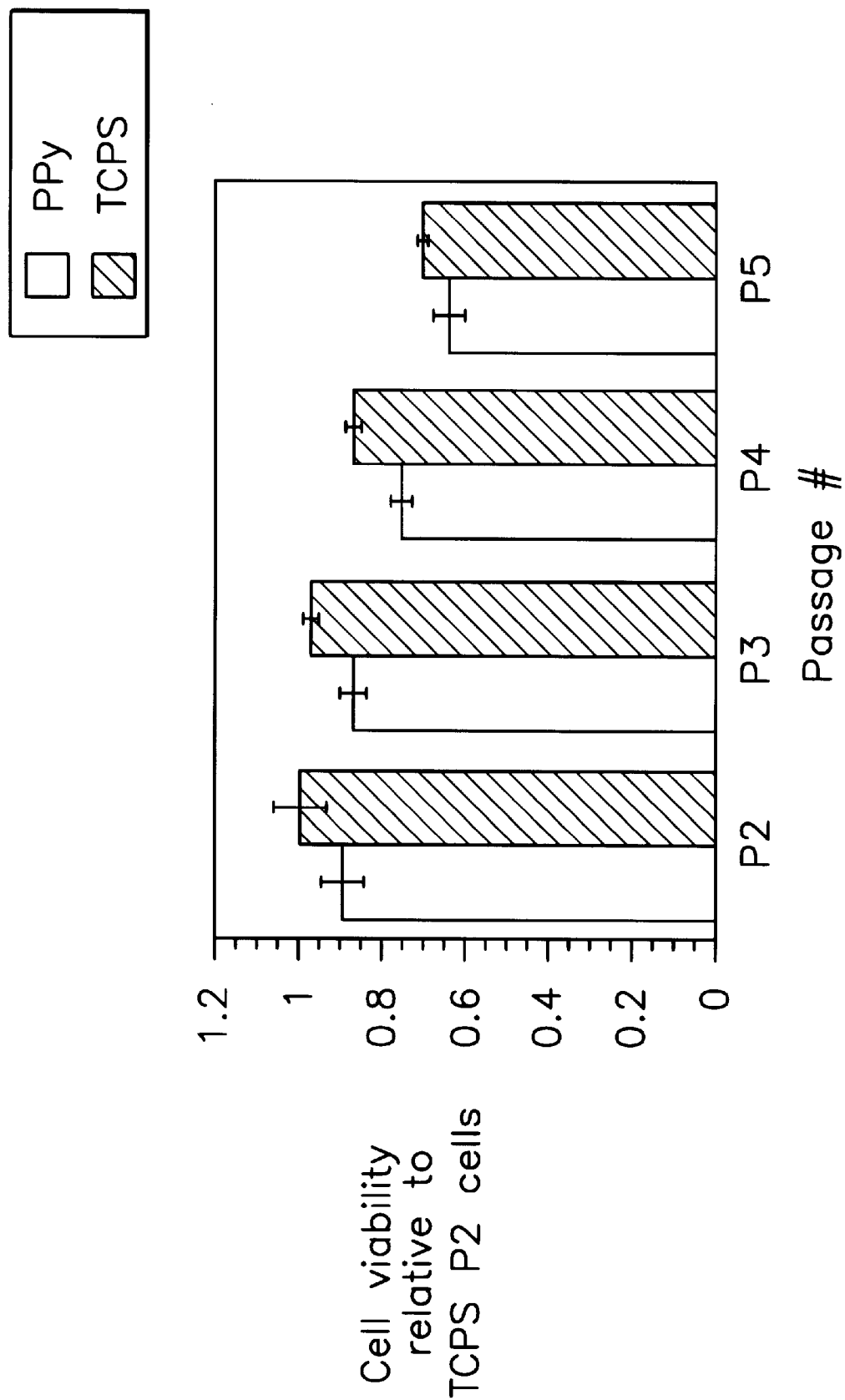
FIG. 21 depicts the effect of passaging on cell viability.

Cells were viewed using a Diaphot phase-contrast microscope (Nikon, Japan). Images were acquired using a CCD video camera and VM-920 monitor from Hitachi (Tokyo, Japan) and were subsequently digitized using NIH Image software and a Scion LG-3 frame grabber (Frederick, Md.).

b. Isolation and Culture of Bone Marrow Stromal Cells (BMSC):

The tibia and femur of 2–3 week old bovine calves were obtained from a local abattoir within 4 hours of slaughter. The bones were cleaned of soft tissue and excised in their diaphyseal region. The contents of the bone marrow cavity were aseptically harvested in Dulbecco's Modified Eagle Medium (DMEM) and 0.5 mM ethylenediamine tetracetic acid (EDTA). Single cell suspensions were made by repeatedly passing the marrow through needles of different gauges (16 to 20). Cells were centrifuged and were resuspended in DMEM supplemented with 10% fetal bovine serum (FBS), 0.1 mM nonessential amino acids (NEAA), 100 U/ml penicillin, 100 mg/L streptomycin and 1 ng/ml fibroblast growth factor-2 (FGF-2). Nucleated cells from the bone marrow, consisting of hematopoietic and stromal populations, were counted using a hemocytometer and plated in 100 mm tissue culture polystyrene Petri dishes at $2 \times 10^6$ cells per dish (approximately $25 \times 10^3$ cells/cm$^2$) in 10 ml of medium. The cells were incubated in a humidified 37° C./5% CO$_2$ incubator. BMSC were selected based on their ability to adhere to the Petri dish; non-adherent hematopoietic cells were removed with culture medium during refeeding. The medium was changed after 3 days and twice per week thereafter, When BMSC became near confluent (approximately 2–3 weeks after the primary culture was established), they were detached using 0.25% trypsin/1 mM EDTA and replated in 100 mm dishes at $3 \times 10^5$ cells per dish. When the cell population reached confluency, these Passage 1 cells were trypsinized, and replated as Passage 2 (P2) cells onto polypyrrole (PPy), indium tin oxide (ITO) and tissue culture polystyrene (TCPS). In all experiments, P2 cells were used, as cell attachment decreases with further passaging (FIG. 21).

Sterile Plexiglass wells (1 cm×1.5 cm inner dimensions) were attached to Ppy films, ITO substrates or TCPS substrates using autoclaved vacuum grease. Each substrate type was tested in duplicate. All wells and substrates were sterilized by UV irradiation in a laminar flow hood for 24 hours prior to seeding.

BMSC (P2) were seeded into the wells at a density of $3\times10^4$ cells/ml per well and then incubated for 48 hours to permit attachment and spreading. Cell viability assay, morphological analysis and alkaline phosphatase assays carried out after 48 hours are described in the following sections.

c. MTT Assay (Cell viability):

MTT (3-[4,5-Dimethylthiazol-2-yl]-2,5-diphenyltetrazolium bromide; Thiazolyl blue) is a water soluble tetrazolium salt, which is converted to an insoluble purple formazan by cleavage of the tetrazolium ring by dehydrogenase enzymes. The cleavage and conversion of the soluble yellow dye to the formazan has been used to develop an assay system for measurement of cell proliferation and cell number. Only active mitochondrial dehydrogenases of living cells will cause the conversion.

After 48 hours, all the wells were evaluated for cell viability on the three substrates: Ppy, ITO and TCPS. A stock solution of MTT at 5 mg/ml was prepared and added to serum-free DMEM, without phenol red, at a volume ratio of 1:20. Culture medium was removed from each of the wells and replaced with 0.5 ml of DMEM-MTT medium. After 4 hours of incubation at 37° C. and 5% $CO_2$, the medium was removed and the converted dye solubilized by adding 1 ml of acidic isopropanol ($6\times10^6$ N HCL in absolute isopropanol). Absorbance of the converted dye was measured at a wavelength of 570 nm with background subtraction at 670 nm on a Perkin-Elmer 533 Fast Scan Spectrophotometer. All cell viability values were normalized to those for TCPS for comparison.

d. Morphological Analysis:

Thin polypyrrole films permitted the use of light microscopy to study BMSC-biomaterial interactions. Cells were viewed using an inverted phase contrast microscope and under a 10× objective. Images were acquired using a CCD video camera and were subsequently digitized using NIH Image software and a Scion LG-3 image capture board.

e. Alkaline Phosphatase (AP) Activity:

Alkaline phosphatase activity is a marker for the osteoblast phenotype. It is used routinely as an indicator for the degree of differentiation seen in BMSC. Alkaline phosphatase activity was determined as the rate of conversion of p-nitrophenyl phosphate to p-nitrophenol. Each assayed well was washed with PBS and 100 ul of 0.01% SDS. After 10 minutes, a prewarmed solution (37° C.) of 0.5 ml substrate (Sigma 104-100) and 0.5 ml alkaline buffer solution were added to each of the wells. After a 15 minute incubation period at 37 ° C., the contents of each well were added to 5 ml of 0.05 N NaOH to quench the reaction and the absorbance was read at 410 nm on a Perkin Elmer 553 Fast Scan Spectrophotometer.

EXAMPLE 3

Cell Culture-Glucocorticoids a. Chemicals and Materials:

Cell culture reagents are described above. Dexamethasone, β-Glycerophosphate and Ascorbic acid were purchased from Sigma and used as received.

b. Methods and Procedures:

BMSC was isolated as described above. P2 Cells were trypsinized and seeded at a density of $5\times10^4$ cells/ml in the sterile Plexiglass wells attached to PPy films, ITO or TCPS. After 48 hours, in dexamethasone test cultures, the original medium was removed and replaced by filtered medium (0.22 um sterile cellulose acetate membrane, Coming, N.Y.) supplemented with 50 ug/ml ascorbic acid, 7 mM β-glycerophosphate and $10^{-8}$ M dexamethasone. Similarly, fresh medium was fed to control cultures on each of the three substrates at the same time. All samples were incubated for another 48 hours prior to MTT<ALP assays and morphological analysis.

EXAMPLE 4

Cell Culture-Electrical Stimulation Studies a. Chemicals and Materials:

Cell culture reagents are described as previously used. Silver wire and gold wire were purchased from Sigma.

b. Methods and Procedures:

BMSC were isolated and described above. Cells were trypsinized and seeded at a density of $5\times10^4$ cells/ml in wells attached to each of the three substrates: PPy, ITO and TCPS.

Figure 22A:
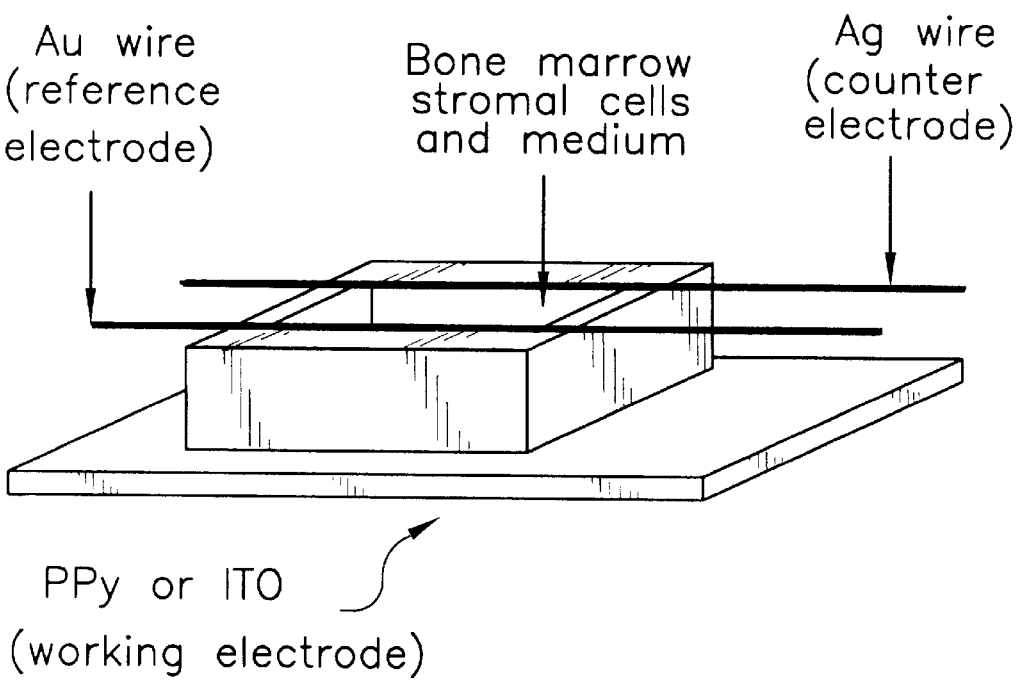
FIGS. 22A and 22B depict plan and top views, respectively, of the assembly for electrical stimulation experiments.
Figure 22B:
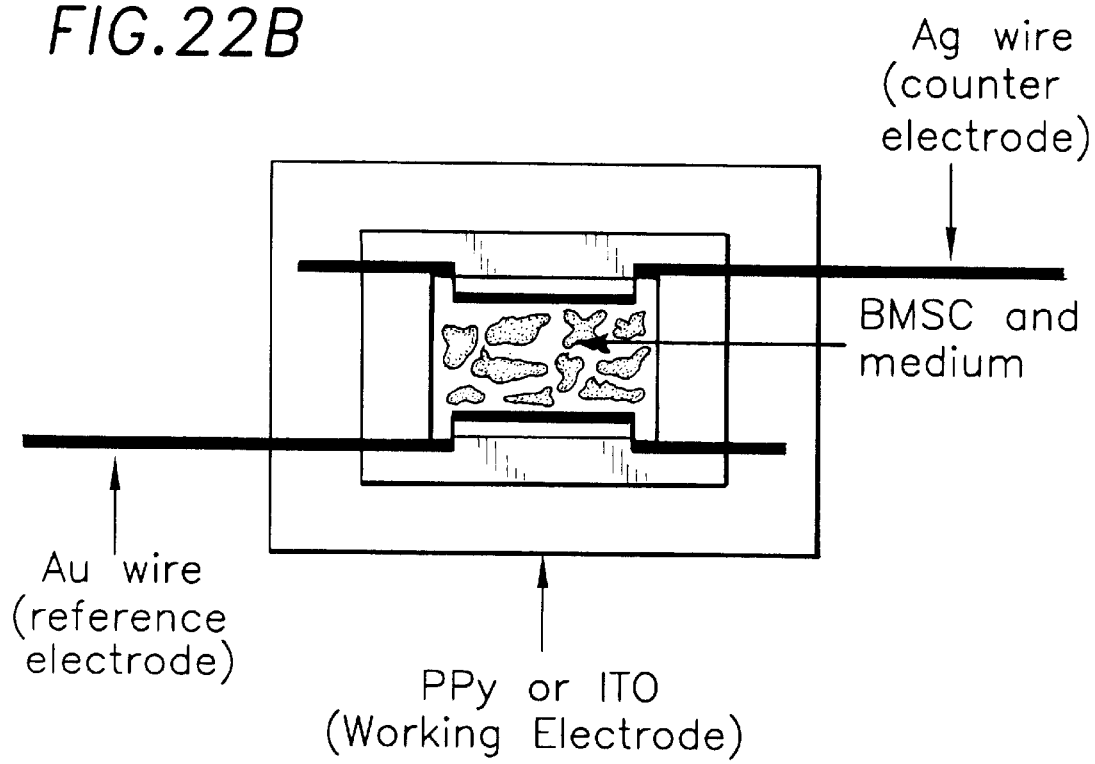

The assembly for electrical stimulation experiments is shown in FIG. 22. The PPy film or ITO slide served as the anode, a gold (Au) wire placed along the length of the well as the cathode and a silver (Ag) wire acted as a quasi-reference electrode. An EG&G Princeton Applied Research Potentiostat/Galvanostat Model 263A (Oakridge, Tenn.) was used as the source of constant potential and cells were incubated at 37° C. and 5% $CO_2$ during the course of the stimulation. All electrically stimulated cells were subjected to a steady potential of 100 mV for 1 hour.

For electrical stimulation (+E) experiments, two conditions were tested for Ppy and ITO substrates: presence of dexamethasone (+E, +Dex) and absence of dexamethasone (+E). For dexamethasone supplemented cultures, dexamethasone was added after 48 hours from the initial seeding (methods as described in Section 5.3) and incubated for another 24 hours prior to electrical stimulation. MTT, ALP assays and morphological evaluation (methods as described in Sections above) were performed 24 hours post stimulation. For (+E) cultures, cells were electrically stimulated at the same time point as for dexamethasone cultures (+E, +Dex) and assayed similarly. Control cultures, without electrical stimulation, in the presence of (+Dex) and absence of dexamethasone (Control), were used to evaluate the effect of electrical stimulation for the two conditions. Each substrate type was tested in duplicate for each condition in three separate experiments.

What we claim is:

1. A method for stimulating one or more biological activities within cells comprising:

directly contacting bone marrow stromal cells with an electroactive substrate, wherein said electroactive substrate has at least one surface of electroactive material, and wherein said electroactive material has attached thereto, or associated therewith, tissue comprising one or more mammalian cells; and applying electromagnetic stimulation at the location of the electroactive substrate, wherein said electromagnetic stimulation is coupled to said electromagnetic material.

2. The method of claim 1, wherein said stimulation of one or more biological activities results from an alteration in the cell membrane resting potential, wherein said electroactive substrate is capable of effecting the alteration in the cell membrane resting potential.

3. The method of claim 2, wherein said stimulation of one or more biological activities is selected from the group consisting of gene expression, cell growth, cell differentiation, cell death, cell signalling, cell signal transduction, and any combination of these biological activities.

4. The method of claim 1, wherein said electromagnetic stimulation is coupled to said electromagnetic material by physical contact.

5. The method of claim 1, wherein said electromagnetic stimulation is coupled to said electromagnetic material by electromagnetic induction.

6. The method of claim 1, wherein said electroactive substrate is two-dimensional.

7. The method of claim 6, wherein said electroactive substrate comprises one or more thin films of said electroactive material.

8. The method of claim 1, wherein said electroactive substrate is three-dimensional.

9. The method of claim 8, wherein said electroactive substrate comprises an electroactive material associated with or attached to a matrix, wherein said matrix is selected from the group consisting of polymers, biological polymers, and celluar solids.

10. The method of claim 1, wherein said electroactive material is an electroactive polymer.

11. The method of claim 10, wherein said polymer is conductive.

12. The method of claim 10, wherein said polymer is a semiconductor.

13. The method of claim 10, wherein said polymer is an ionically conducting polymer.

14. The method of claim 10, wherein said electroactive polymer is selected from the group consisting of polypyrrole, poly(p-phenylene), poly(p-phenylene-vinylene), poly(thiophene), poly(aniline), poly(porphyrin), and poly(heme).

15. A method for stimulating one or more biological activities within a cell, comprising:
   providing a composition of bone marrow stromal cells and an electroactive substrate, wherein said electroactive substrate has at least one surface of electroactive material, and wherein said cells are attached directly thereto;
   applying electromagnetic stimulation to said composition, wherein said electromagnetic stimulation is coupled to said electroactive material; and
   contacting said composition with a mammalian tissue, wherein the step of contacting may be performed before or after the step of applying.

16. The method of claim 15, wherein said stimulation of one or more biological activities results from an alteration in the cell membrane resting potential, wherein said electroactive substrate is capable of effecting the alteration in the cell membrane resting potential.

17. The method of claim 16, wherein said stimulation of one or more biological activities is selected from the group consisting of gene expression, cell growth, cell differentiation, cell signal transduction, cell signalling, and any combination of these biological activities.

18. The method of claim 15, wherein said electromagnetic stimulation is coupled to said electromagnetic material by physical contact.

19. The method of claim 15, wherein said electromagnetic stimulation is coupled to said electromagnetic material by electromagnetic induction.

20. The method of claim 15, wherein said electroactive substrate is two-dimensional.

21. The method of claim 20, wherein said electroactive substrate comprises one or more thin films of said electroactive material.

22. The method of claim 15, wherein said electroactive substrate is three-dimensional.

23. The method of claim 22, wherein said electroactive substrate comprises an electroactive material associated with or attached to a matrix, wherein said matrix is selected from the group consisting of polymers, biological polymers, and cellular solids.

24. The method of claim 15; wherein said electroactive material is an electroactive polymer.

25. The method of claim 24, wherein said polymer is conductive.

26. The method of claim 24, wherein said polymer is a semiconductor.

27. The method of claim 24, wherein said polymer is an ionically conducting polymer.

28. The method of claim 24, wherein said electroactive polymer is selected from the group consisting of polypyrrole, poly(p-phenylene), poly(p-phenylene-vinylene), poly(thiophene), poly(aniline), poly(porphyrin), and poly(heme).

29. A method for stimulating one or more biological activities within a cell, comprising:
   providing a composition of bone marrow stromal cells and an electroactive substrate, wherein said electroactive substrate has at least one surface of electroactive material, and wherein said cells are attached directly thereto;
   applying electromagnetic stimulation to said composition, wherein said electromagnetic stimulation is coupled to said electroactive material;
   removing said stimulated cells from said electromagnetic material; and
   contacting the stimulated cells with a mammalian tissue, wherein the step of contacting may be performed before or after the step of applying or after the step of removing.

30. The method of claim 29, wherein said stimulation of one or more biological activities results from an alteration in the cell membrane resting potential, wherein said electroactive substrate is capable of effecting the alteration in the cell membrane resting potential.

31. The method of claim 30, wherein said stimulation of one or more biological activities is selected from the group consisting of gene expression, cell growth, cell differentiation, cell signal transduction, cell signalling, and any combination of these biological activities.

32. The method of claim 29, wherein said electromagnetic stimulation is coupled to said electromagnetic material by physical contact.

33. The method of claim 29, wherein said electromagnetic stimulation is coupled to said electromagnetic material by electromagnetic induction.

34. The method of claim 29, wherein said electroactive substrate is two-dimensional.

35. The method of claim 34, wherein said electroactive substrate comprises one or more thin films of said electroactive material.

36. The method of claim 29, wherein said electroactive substrate is three-dimensional.

37. The method of claim 36, wherein said electroactive substrate comprises an electroactive material associated with or attached to a matrix, wherein said matrix is selected from the group consisting of polymers, biological polymers, and cellular solids.

38. The method of claim 29; wherein said electroactive material is an electroactive polymer.

39. The method of claim 38, wherein said polymer is conductive.

40. The method of claim 38, wherein said polymer is a semiconductor.

41. The method of claim 38, wherein said polymer is an ionically conducting polymer.

42. The method of claim 38, wherein said electroactive polymer is selected from the group consisting of polypyrrole, poly(p-phenylene), poly(p-phenylenevinylene), poly(thiophene), poly(aniline), poly(porphyrin), and poly(heme).

43. A method for stimulating one or more biological activities within a cell, comprising;
   providing a composition of bone marrow stromal cells and an electroactive substrate, wherein said electroactive substrate has at least one surface of electroactive material, and wherein said cells are attached directly thereto;
   contacting said composition with mammalian tissue; and
   applying electromagnetic stimulation to said composition, wherein said electromagnetic stimulation is coupled to said electroactive material.

44. The method of claim 43, wherein said stimulation of one or more biological activities results from an alteration in the cell membrane resting potential, wherein said electroactive substrate is capable of effecting the alteration in the cell membrane resting potential.

45. The method of claim 44, wherein said stimulation in one or more biological activities is selected from the group consisting of gene expression, cell growth, cell signal transduction, cell differentiation, cell signalling, cell death and any combination of these biological activities.

46. The method of claim 43, wherein said electromagnetic stimulation is coupled to said electromagnetic material by physical contact.

47. The method of claim 43, wherein said electromagnetic stimulation is coupled to said electromagnetic material by electromagnetic induction.

48. The method of claim 43, wherein said electroactive substrate is two-dimensional.

49. The method of claim 48, wherein said electroactive substrate comprises one or more thin films of said electroactive material.

50. The method of claim 43, wherein said electroactive substrate is three-dimensional.

51. The method of claim 50, wherein said electroactive substrate comprises an electroactive material associated with or attached to a matrix, wherein said matrix is selected from the group consisting of polymers, biological polymers, and cellular solids.

52. The method of claim 43, wherein said electroactive material is in electroactive polymer.

53. The method of claim 52, wherein said polymer is conductive.

54. The method of claim 52, wherein said polymer is a semiconductor.

55. The method of claim 52, wherein said polymer is an ionically conducting polymer.

56. The method of claim 52, wherein said electroactive polymer is selected from the group consisting of polypyrrole, poly(p-phenylene), poly(p-phenylenevinylene), poly(thiophene), poly(aniline), poly(porphyrin), and poly(heme).

57. A system for stimulating one or more biological activities of cells, comprising:
   a composition comprising an electroactive substrate, wherein said electroactive substrate has at least one surface of electroactive material, and wherein said electroactive material has attached directly thereto bone marrow stromal cells; and
   an apparatus for applying electromagnetic energy at the desired location.

58. The system of claim 57, wherein said electroactive substrate is two-dimensional.

59. The system of claim 57, wherein said electroactive substrate is three-dimensional.

* * * * *